United States Patent
Azar et al.

(10) Patent No.: US 11,331,096 B2
(45) Date of Patent: May 17, 2022

(54) SURGICAL METHOD AND SYSTEM FOR PERFORMING THE SAME

(71) Applicants: Toufic Azar, Montreal (CA); RenZo Cecere, Mont-Royal (CA)

(72) Inventors: Toufic Azar, Montreal (CA); Renzo Cecere, Mont-royal (CA); Robert Forestell, Montreal (CA)

(73) Assignee: MEACOR, INC., Ayer, MA (US)

( * ) Notice: Subject to any disclaimer, the term of this patent is extended or adjusted under 35 U.S.C. 154(b) by 368 days.

(21) Appl. No.: 16/658,414

(22) Filed: Oct. 21, 2019

(65) Prior Publication Data

US 2020/0046344 A1 Feb. 13, 2020

Related U.S. Application Data

(63) Continuation of application No. 15/531,622, filed as application No. PCT/IB2015/059806 on Dec. 19, 2015, now Pat. No. 10,512,460.

(Continued)

(51) Int. Cl.
*A61B 17/068* (2006.01)
*A61B 17/04* (2006.01)
(Continued)

(52) U.S. Cl.
CPC ........ *A61B 17/068* (2013.01); *A61B 17/0469* (2013.01); *A61B 17/064* (2013.01);
(Continued)

(58) Field of Classification Search
CPC . A61B 17/068; A61B 17/0469; A61B 17/064; A61B 18/02; A61B 2017/00243; A61F 2/2445; A61F 2/2466; A61F 7/12
See application file for complete search history.

(56) References Cited

U.S. PATENT DOCUMENTS

| 5,810,851 A | 9/1998 | Yoon |
| 6,280,441 B1 | 8/2001 | Ryan |

(Continued)

FOREIGN PATENT DOCUMENTS

| WO | 9607360 | 3/1996 |
| WO | 0158397 | 8/2001 |

(Continued)

OTHER PUBLICATIONS

Written Opinion of the International Searching Authority issued by the World Intellectual Property Organization dated Apr. 25, 2016 for PCT application PCT/IB2015/059806 from which the present application claims priority.

(Continued)

*Primary Examiner* — Thomas McEvoy

(57) ABSTRACT

A method using a guide to assist in insertion of a helicoidal member in a target biological tissue. The method includes abutting a substantially longitudinally extending portion of the guide against a target tissue exposed surface with the helicoidal member mounted thereto so that at least a portion of the guide is inserted in a helicoidal member passageway substantially parallel to a helicoidal member longitudinal axis of the helicoidal member; adhering the substantially longitudinally extending portion of the guide to the target tissue exposed surface with the helicoidal member longitudinal axis substantially parallel to the target tissue exposed surface; and advancing the helicoidal member in the target biological tissue in a substantially helicoidal movement with the guide remaining substantially fixed relative to the target biological tissue.

43 Claims, 16 Drawing Sheets

Related U.S. Application Data

Figure 1:
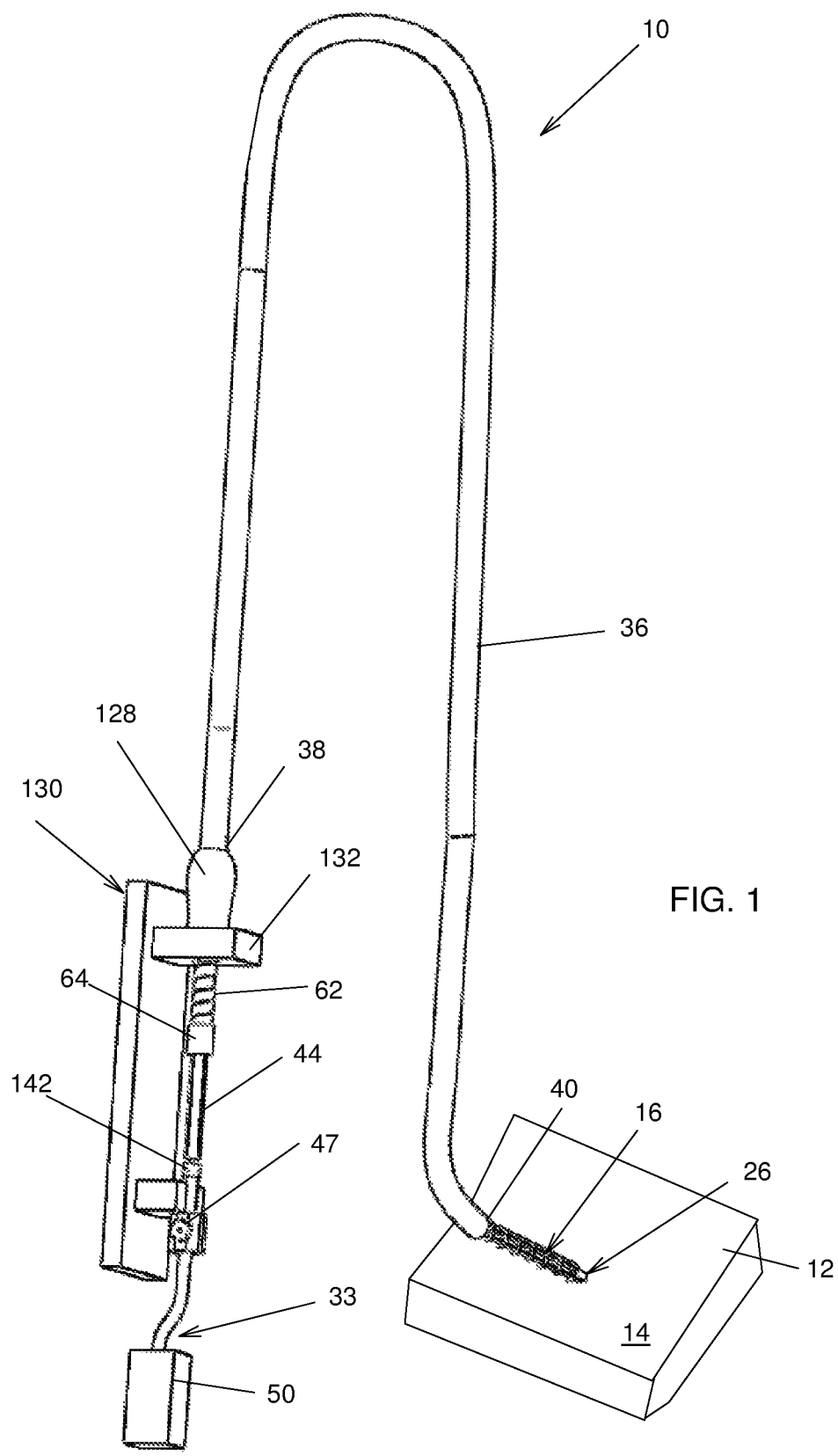

(60) Provisional application No. 62/186,708, filed on Jun. 30, 2015, provisional application No. 62/094,151, filed on Dec. 19, 2014.

(51) Int. Cl.

| | |
|---|---|
| *A61F 2/24* | (2006.01) |
| *A61B 17/064* | (2006.01) |
| *A61B 18/02* | (2006.01) |
| *A61F 7/12* | (2006.01) |
| *A61B 17/00* | (2006.01) |
| *A61B 17/06* | (2006.01) |
| *A61B 18/00* | (2006.01) |
| *A61B 17/30* | (2006.01) |

(52) U.S. Cl.
CPC ............ *A61B 18/02* (2013.01); *A61F 2/2445* (2013.01); *A61F 2/2466* (2013.01); *A61F 7/12* (2013.01); *A61B 2017/00243* (2013.01); *A61B 2017/00566* (2013.01); *A61B 2017/00783* (2013.01); *A61B 2017/0409* (2013.01); *A61B 2017/0441* (2013.01); *A61B 2017/0498* (2013.01); *A61B 2017/0649* (2013.01); *A61B 2017/06052* (2013.01); *A61B 2017/06076* (2013.01); *A61B 2017/306* (2013.01); *A61B 2018/00291* (2013.01); *A61B 2018/0212* (2013.01); *A61B 2018/0287* (2013.01); *A61F 2007/126* (2013.01); *A61F 2230/0091* (2013.01)

(56) References Cited

U.S. PATENT DOCUMENTS

| | | |
|---|---|---|
| 6,524,338 B1 | 2/2003 | Gundry |
| 6,626,917 B1 | 9/2003 | Craig |
| 7,972,370 B2 | 7/2011 | Douk et al. |
| 8,241,351 B2 | 8/2012 | Cabiri |
| 8,696,689 B2 | 4/2014 | Tuval et al. |
| 8,771,292 B2 | 7/2014 | Allen et al. |
| 8,906,039 B2 | 12/2014 | Crainich |
| 8,939,937 B2 | 1/2015 | Shanley |
| 8,940,044 B2 | 1/2015 | Hammer et al. |
| 9,078,633 B2 | 7/2015 | Belson et al. |
| 9,180,008 B2 | 11/2015 | Yellin et al. |
| 9,186,176 B2 | 11/2015 | Litvack et al. |
| 2002/0147446 A1 | 10/2002 | Ein-Gal |
| 2003/0130650 A1 | 7/2003 | Yaron |
| 2004/0181287 A1* | 9/2004 | Gellman .................. A61F 2/88 623/23.66 |
| 2005/0065601 A1 | 3/2005 | Lee et al. |
| 2006/0173517 A1 | 8/2006 | Gross |
| 2006/0206203 A1 | 9/2006 | Yang |
| 2006/0253127 A1 | 11/2006 | Bjerken |
| 2007/0027533 A1 | 2/2007 | Douk |
| 2007/0244556 A1 | 10/2007 | Rafiee et al. |
| 2009/0105816 A1 | 4/2009 | Olsen |
| 2009/0275960 A1 | 11/2009 | Provenza |
| 2010/0010625 A1 | 1/2010 | McCarthy |
| 2011/0112569 A1 | 5/2011 | Friedman et al. |
| 2011/0190811 A1 | 8/2011 | Shanley |
| 2012/0010645 A1 | 1/2012 | Feld |
| 2012/0071868 A1 | 3/2012 | Fischer |
| 2012/0071920 A1 | 3/2012 | Shanley et al. |
| 2012/0277853 A1 | 11/2012 | Rothstein |
| 2014/0207154 A1 | 7/2014 | Bielefeld |
| 2015/0025623 A1 | 1/2015 | Granada et al. |

FOREIGN PATENT DOCUMENTS

| | | |
|---|---|---|
| WO | 2007098212 | 8/2007 |
| WO | 2013147990 | 3/2013 |
| WO | 2014197632 | 12/2014 |
| WO | 2015124632 | 2/2015 |

OTHER PUBLICATIONS

International Search Report issued by the World Intellectual Property Organization dated Apr. 25, 2016 for PCT application PCT/IB2015/059806 from which the present application claims priority.

* cited by examiner

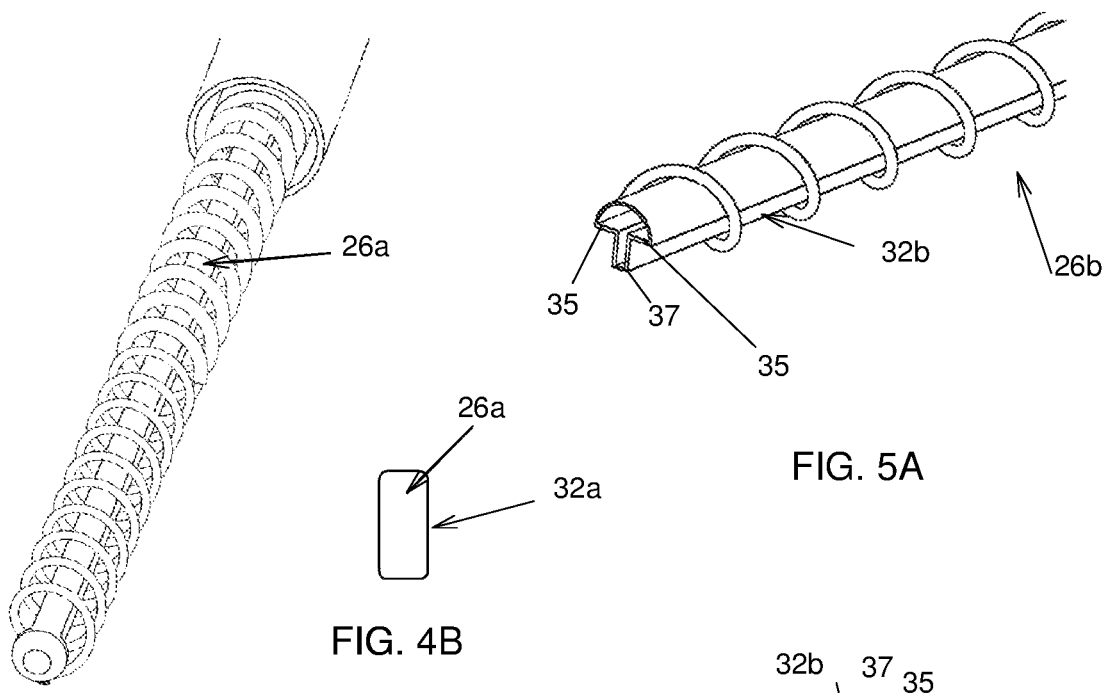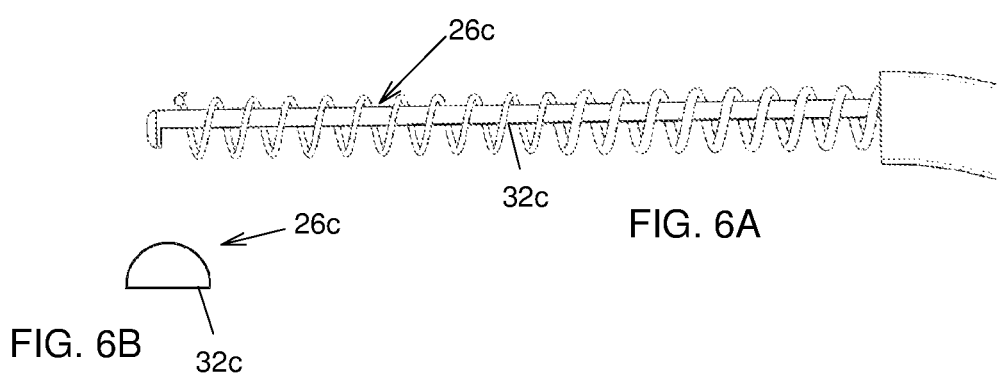

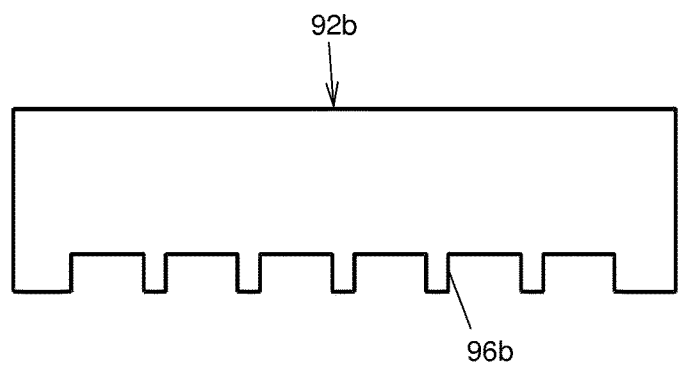
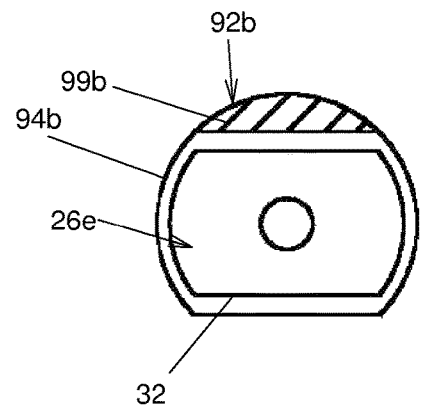
FIG. 15A  FIG. 15B
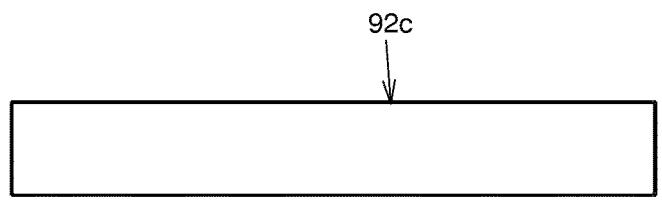
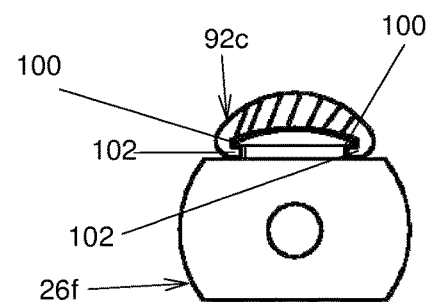
FIG. 16A  FIG. 16B
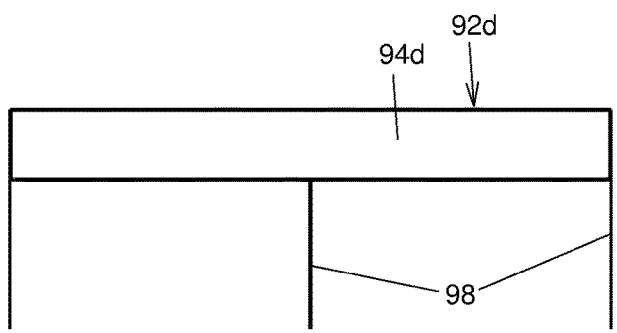
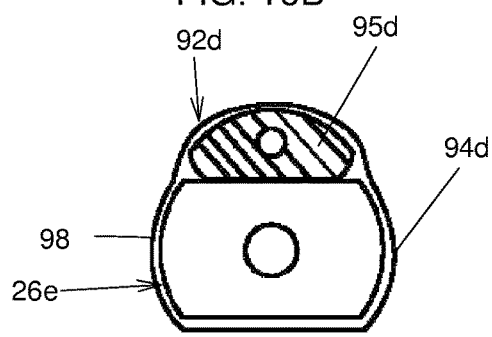
FIG. 17A  FIG. 17B

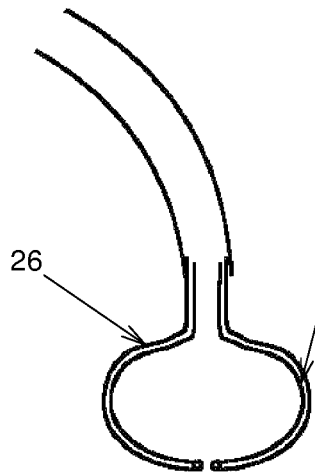 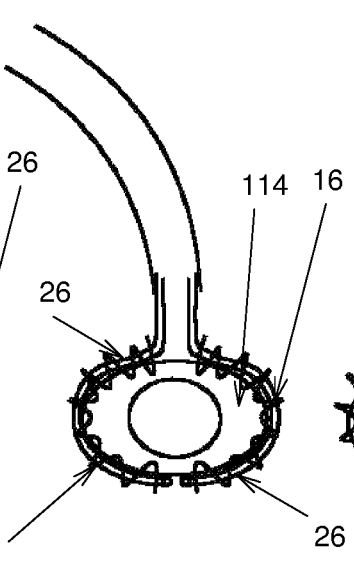 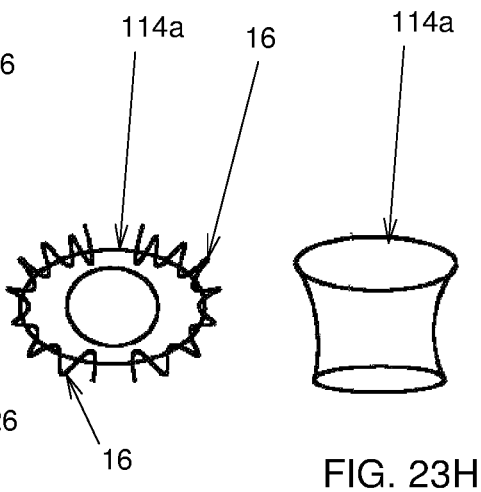 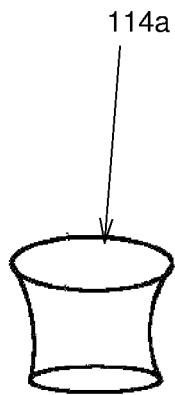
FIG. 23E    FIG. 23F    FIG. 23G    FIG. 23H
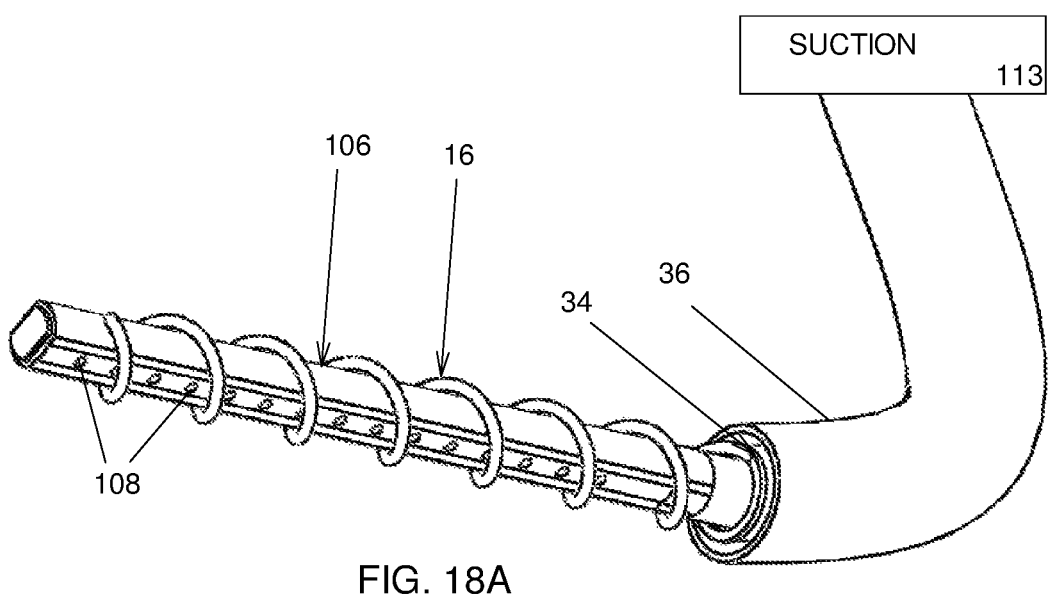
FIG. 18A
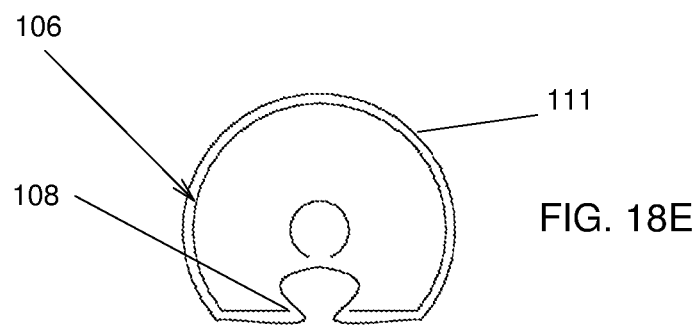
FIG. 18E

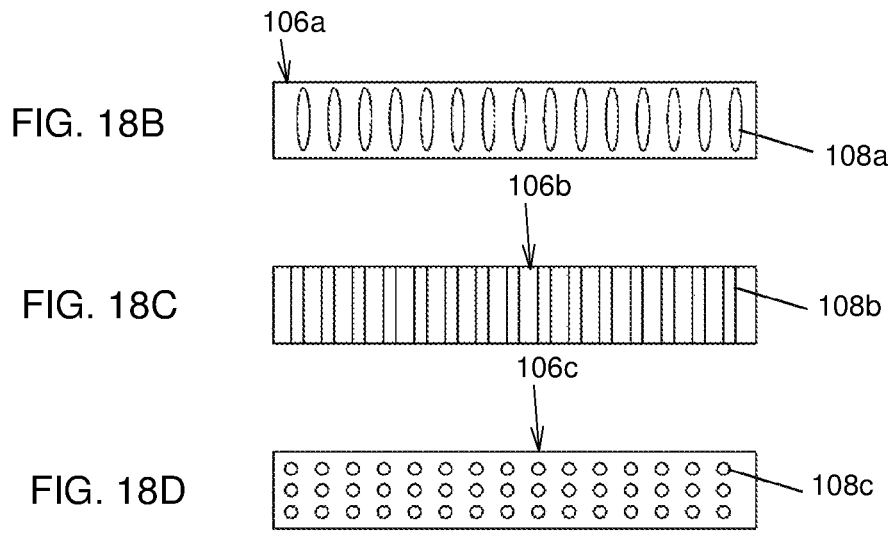
FIG. 18B
FIG. 18C
FIG. 18D
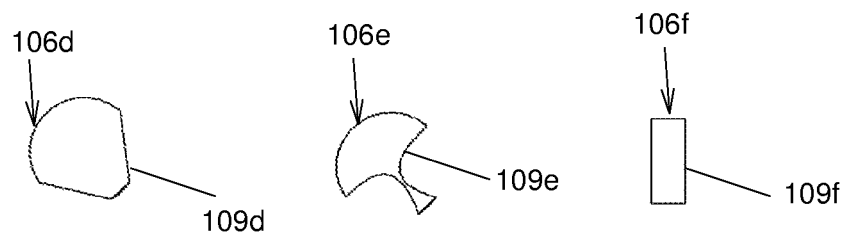
FIG. 19A  FIG. 19B  FIG. 19C
FIG. 19D  FIG. 19E  FIG. 19F
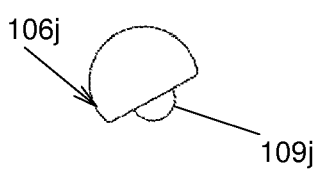
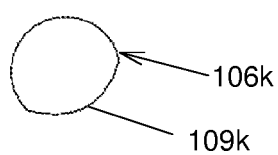
FIG. 19G  FIG. 19H

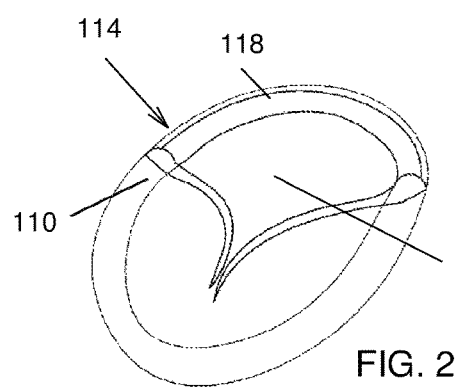
FIG. 23A
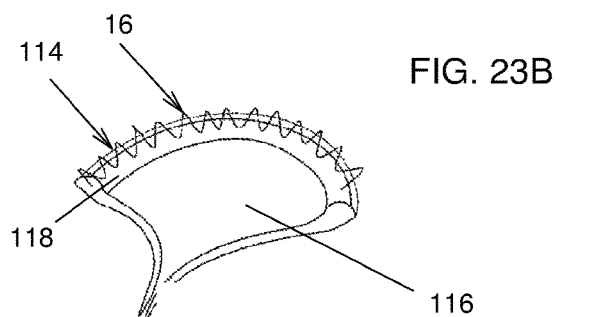
FIG. 23B
FIG. 23C
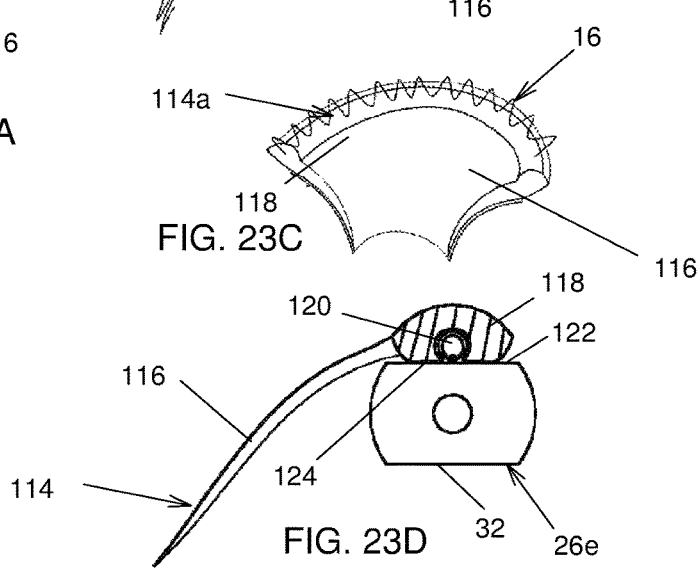
FIG. 23D
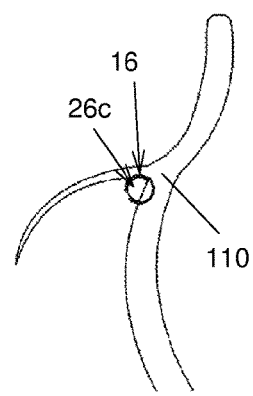
FIG. 24E
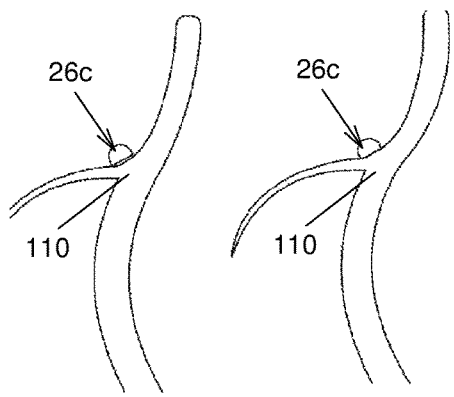
FIG. 24A        FIG. 24B        FIG. 24C        FIG. 24D

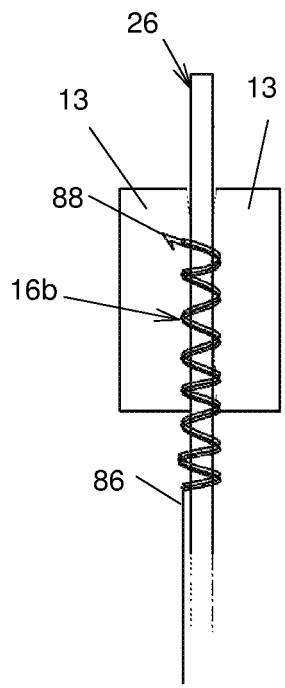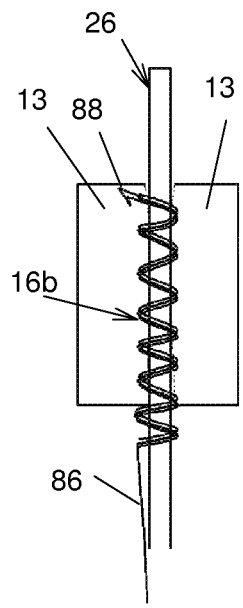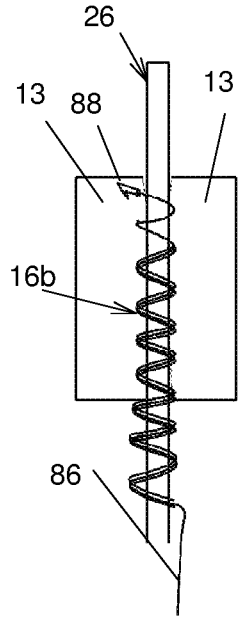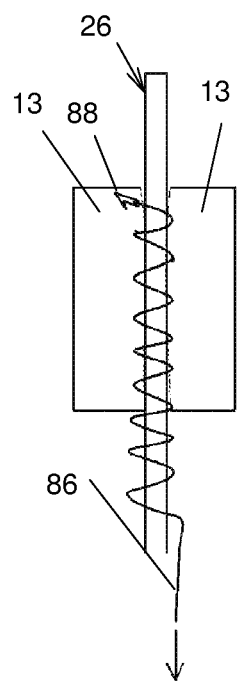
FIG. 25A  FIG. 25B  FIG. 25C  FIG. 25D
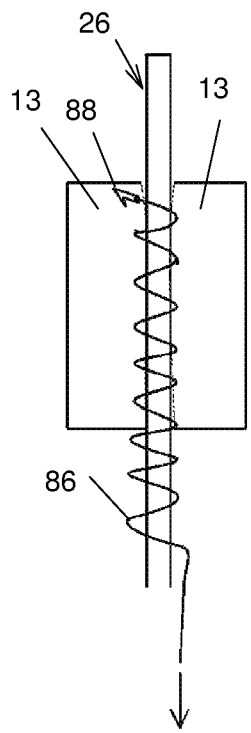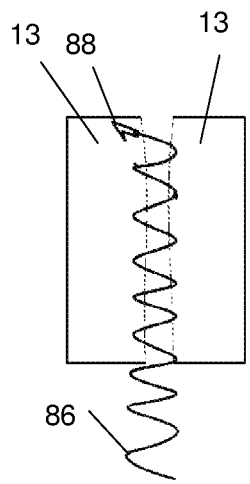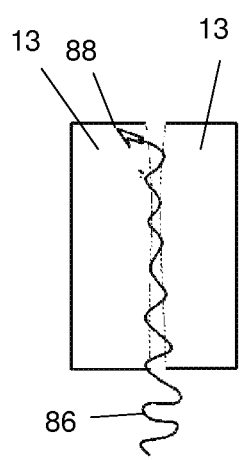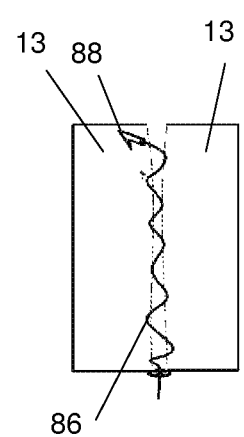
FIG. 25E  FIG. 25F  FIG. 25G  FIG. 25H

SURGICAL METHOD AND SYSTEM FOR PERFORMING THE SAME

FIELD OF THE INVENTION

The present invention relates to general field of surgery. More specifically, the present invention is concerned with a surgical method and a system for performing the same.

BACKGROUND

Some surgical procedures involve insertion of a helicoidal member into tissue, either in the form of an anchor that remains in place at the end of the procedure, or as a needle that is used to insert a suture thread. The helicoidal member is inserted by rotating it about its longitudinal axis. Once the helicoidal member has its tip inserted in the tissue, the rotation advances the helicoidal member in the tissue as the tip moves forward with the rotation. Helicoidal members may be inserted so that their longitudinal axis is perpendicular to a tissue surface to penetrate. In such cases, the forces exerted on the instrument used to insert the anchor help in maintaining the instrument fixed relative to the tissue surface during the procedure. If needed, the instrument may also be fixed relative to the tissue by securing the tip of the instrument to the tissue.

In some procedures it would be advantageous to insert the helicoidal member in the tissue with its longitudinal axis parallel to the tissue surface. After insertion, part of each coil making the helicoidal member is then outside of the tissue, adjacent the tissue surface, and the remainder of the helicoidal member is embedded in the tissue. Insertion of the helicoidal member, especially in transcatheter procedures, is difficult to perform as the instrument needs to be kept fixed at a predetermined location, at least for the first few turns of the helicoidal member during insertion. However, the various forces and torques exerted on the helicoidal member and the instrument used for insertion make immobilization of the instrument very difficult.

Mitral valve regurgitation (MR) is a functional heart disease under which the valve does not close completely and causes blood to leak back into the left atrium. This condition increases the workload on the heart and, if left untreated, can lead to irreversible heart damage, cardiac arrhythmia and congestive heart failure. Currently, mitral valve repair, as the intervention is called, requires open heart surgery with cardiopulmonary bypass. Under such conditions, the patient is subjected to intra- and post-operative trauma that can result in mortality increase and that can prevent high-risk individuals from undergoing the intervention. Hence the need to develop alternative procedures such as minimally invasive percutaneous interventions, which would greatly reduce the trauma and risks associated with conventional surgery, resulting in an increase of the number of potential candidates for repair, while significantly cutting patient's recovery times from weeks to days. There have been attempts to perform such surgery with helicoidal anchors inserted at the periphery of the valve, but they have failed, at least in part because of the problem of instrument immobilization described hereinabove.

Against this background, there exists a need in the industry to provide novel surgical methods and systems for performing the same in which helicoidal members are inserted in tissues. An object of the present invention is therefore to provide such improved methods and systems.

SUMMARY OF THE INVENTION

In a first broad aspect, the invention provides a system for performing a surgical procedure in a target biological tissue, the target biological tissue defining a target tissue exposed surface, the system including: a substantially helicoidal member, the helicoidal member defining a helicoidal member longitudinal axis and substantially longitudinally opposed helicoidal member proximal and distal ends; a substantially elongated guide positionable so as to be extending at least partially through the helicoidal member along the helicoidal member longitudinal axis, the guide defining a guide tip and a guide peripheral surface extending substantially longitudinally from the guide tip, the guide peripheral surface having a peripheral surface cooled portion covering at least part of the guide peripheral surface; a cooling subsystem operatively coupled to the guide for selectively cooling the peripheral surface cooled portion to a temperature sufficiently low to cause adhesion between the guide and the target biological tissue; a driver, the helicoidal member being mounted to the driver at the helicoidal member proximal end, the driver being operative for selectively simultaneously rotating the helicoidal member along the helicoidal member longitudinal axis and allowing the helicoidal member to advance along the guide in a distally oriented direction; wherein, in operation, when the cooling subsystem cools the peripheral surface cooled portion and the latter is positioned to abut against the target tissue exposed surface, the peripheral surface cooled portion adheres to the target tissue exposed surface so that the driver can operated to drive the helicoidal member into the target biological tissue by rotating the helicoidal member and advancing the helicoidal member along the guide with the peripheral surface cooled portion remaining fixed relative to the target biological tissue.

The invention may also provide a system wherein the helicoidal member is selectively detachable from the driver.

The invention may also provide a system wherein the driver includes a driver lock movable between a locked configuration and an unlocked configuration, wherein, in the locked configuration, the helicoidal member is locked to the driver, and, in the unlocked configuration, the helicoidal member is detachable from the driver.

The invention may also provide a system wherein the driver includes a substantially helicoidal thread configured and sized for receiving part of the helicoidal member at the helicoidal member proximal end.

The invention may also provide a system wherein the helicoidal member is provided with at least one notch substantially longitudinally extending substantially adjacent the helicoidal member proximal end and the driver lock includes a pin insertable in the notch when the helicoidal member is operatively secured to the driver in the helicoidal thread, the pin being selectively removable from the notch, the pin being inserted in the notch in the locked configuration and the pin being removed from the notch in the unlocked configuration.

The invention may also provide a system wherein the lock includes a wire secured to the pin and the pin is mounted in a substantially longitudinally extending pin receiving passageway intersecting the helicoidal threads, the pin being removable from the pin receiving passageway by pulling on the wire. The pin may be flexible or rigid. In some embodiments, the pin and wire extend integrrally from each other.

The invention may also provide a system wherein the cooling subsystem includes a coolant passageway having a portion thereof substantially adjacent to the peripheral surface cooled portion, the coolant passageway being configured for circulating a coolant therethrough to cool the peripheral surface cooled portion.

The invention may also provide a system wherein the cooling subsystem further includes a coolant source in a fluid communication relationship with the coolant passageway for providing cooled coolant thereto.

The invention may also provide a system wherein the guide is hollow and the cooling subsystem includes a coolant tube positioned at least partially in the guide, the coolant tube defining at least part of the coolant passageway.

The invention may also provide a system wherein the guide is closed at guide tip and the coolant tube is provided with at least one coolant tube outlet located in the guide substantially adjacent the peripheral surface cooled portion, the coolant tube having at least a portion thereof that is spaced apart from the guide so that coolant can be circulated from the coolant tube, through the coolant outlet and between the coolant tube and the guide.

The invention may also provide a system further comprising a substantially elongated catheter defining substantially opposed catheter proximal and distal ends and a catheter lumen extending therebetween, the guide being partially provided in the catheter lumen and protruding therefrom at the catheter distal end.

The invention may also provide a system further comprising a hook removably mountable to the helicoidal member and a suture thread secured to the hook.

The invention may also provide a system wherein the helicoidal member is made of a hollow tube, the suture thread extending through the hollow tube and the hook engaging the hollow tube at the helicoidal member distal end.

The invention may also provide a system wherein the driver is further operative for retracting the helicoidal member in a proximally oriented direction and the hook is removable from the helicoidal member when the hook is pulled.

The invention may also provide a system wherein the peripheral surface cooled portion is at least partially substantially flat.

The invention may also provide a system further comprising an insert mounted to the guide, the insert and guide being longitudinally movable relative to each other.

The invention may also provide a system wherein the insert includes a substantially resiliently deformable piece of material provided opposed to the peripheral surface cooled portion.

The invention may also provide a system wherein the insert is made of a foam.

The invention may also provide a system wherein the insert includes a substantially tubular membrane positioned over the guide peripheral surface, the membrane being provided with apertures in register with the peripheral surface cooled portion.

The invention may also provide a system wherein the insert includes a membrane positioned over the guide peripheral surface opposed to the peripheral surface cooled portion so that the peripheral surface cooled portion is free of the membrane.

The invention may also provide a system further comprising attachment loops securing the membrane to the guide, the attachment loops extending circumferentially around the guide.

The invention may also provide a system wherein the guide defines a pair of substantially longitudinally extending mounting grooves and the insert defines a pair of substantially longitudinally extending mounting rods each mounted in a respective one of the mounting grooves.

The invention may also provide a system wherein the helicoidal member is inserted through the insert.

The invention may also provide a system wherein the helicoidal member has the same shape before and after insertion in the target biological tissue.

The invention may also provide a system wherein the helicoidal member includes a shape memory material, the helicoidal member changing between a helicoidal member first configuration and a helicoidal member second configuration at a transition temperature, the transition temperature being between 20 C and 37 C, but other values are within the scope of the invention.

The invention may also provide a system wherein the helicoidal member first and second configurations have different pitches.

The invention may also provide a system wherein the helicoidal member has a pitch that varies between the helicoidal member proximal and distal ends.

The invention may also provide a system wherein the pitch is larger at the helicoidal member distal end than at the helicoidal member proximal end.

In another broad aspect, the invention provides a surgical method using a guide to assist in insertion of a helicoidal member in a target biological tissue, the target biological tissue defining a target tissue exposed surface, the helicoidal member defining a helicoidal member longitudinal axis and substantially longitudinally opposed helicoidal member proximal and distal ends, a helicoidal member passageway extending longitudinally between the helicoidal member proximal and distal ends, the guide being substantially elongated and defining a guide tip, the method including: abutting a substantially longitudinally extending portion of the guide against the target tissue exposed surface with the helicoidal member mounted thereto so that at least a portion of the guide is inserted in the helicoidal member passageway substantially parallel to the helicoidal member longitudinal axis; adhering the substantially longitudinally extending portion of the guide to the target tissue exposed surface with the helicoidal member longitudinal axis substantially parallel to the target tissue exposed surface; and advancing the helicoidal member in the target biological tissue in a substantially helicoidal movement with the guide remaining substantially fixed relative to the target biological tissue.

The invention may also provide a method wherein adhering the substantially longitudinally extending portion of the guide to the target tissue exposed surface includes cooling at least part of the guide to a predetermined temperature, the predetermined temperature being low enough to cause cryoadhesion between the substantially longitudinally extending portion of the guide and the target tissue exposed surface.

The invention may also provide a method wherein the predetermined temperature is low enough to allow cryoadhesion, but remains high enough and is applied for a duration short enough that substantially no irreversible physiological damages are caused to the target biological tissue.

The invention may also provide a method wherein the predetermined temperature is between 0 and −40 C.

The invention may also provide a method wherein the guide includes suction apertures in the substantially longitudinally extending portion of the guide and wherein adhering the substantially longitudinally extending portion of the guide to the target tissue exposed surface includes exerting a suction through the suction apertures.

The invention may also provide a method wherein the helicoidal member is between the guide tip and the substantially longitudinally extending portion of the guide before adhering the substantially longitudinally extending portion of the guide to the target tissue exposed surface.

The invention may also provide a method wherein the substantially longitudinally extending portion of the guide is between the guide tip and helicoidal member before adhering the substantially longitudinally extending portion of the guide to the target tissue exposed surface.

The invention may also provide a method wherein the substantially longitudinally extending portion of the guide and the helicoidal member have at least portions thereof substantially in register with each other before adhering the substantially longitudinally extending portion of the guide to the target tissue exposed surface.

The invention may also provide a method further comprising detaching the guide from the target tissue exposed surface with the helicoidal member remaining in the target biological tissue and removing the guide from within the helicoidal member passageway.

The invention may also provide a method further comprising delivering an insert while advancing the helicoidal member so that when the helicoidal member remains in the target biological tissue, the helicoidal member engages the insert.

The invention may also provide a method wherein the insert includes a membrane.

The invention may also provide a method wherein the insert includes a resiliently deformable material.

The invention may also provide a method further comprising delivering a prosthesis while advancing the helicoidal member so that when the helicoidal member remains in the target biological tissue, the prosthesis is secured to the target biological tissue by the helicoidal member.

The invention may also provide a method wherein the prosthesis includes a cardiac valve.

The invention may also provide a method wherein the helicoidal member supports a distally provided hook to which a suture thread is secured, the hook being removable from the helicoidal member, the method further comprising using the helicoidal member to insert the suture thread in a helicoidal configuration in the target biological tissue; withdrawing the helicoidal member from the target biological tissue with the hook hooking the target biological tissue so that the hook and suture thread remain in the target biological tissue; and pulling on the suture thread to tighten the suture thread.

The invention may also provide a method further comprising positioning the guide at a predetermined location along the target tissue exposed surface before adhering the substantially longitudinally extending portion of the guide to the target tissue exposed surface.

The invention may also provide a method further comprising adjusting the shape of the guide before adhering the substantially longitudinally extending portion of the guide to the target tissue exposed surface.

The invention may also provide a method further comprising inserting a catheter in a mammal in which the target biological tissue is located so that a catheter distal tip of the catheter is substantially adjacent the target tissue exposed surface; and advancing the guide in the catheter until at least part of the guide protrudes from the guide.

The invention may also provide a method wherein the target biological tissue is a valve annulus.

The invention may also provide a method comprising implanting at least two of the helicoidal members around the valve annulus and tightening the valve annulus by pulling the at least two helicoidal member towards each other.

The invention may also provide a method wherein the method includes implanting the helicoidal member around the valve annulus and tightening the valve annulus by reducing a radius of curvature of the helicoidal member.

The invention may also provide a method wherein the valve annulus is a mitral valve annulus.

The invention may also provide a method wherein the helicoidal member has the same shape before and after insertion in the target biological tissue.

The invention may also provide a method wherein the helicoidal member includes a shape memory material, the helicoidal member changing between a helicoidal member first configuration and a helicoidal member second configuration at a transition temperature, the transition temperature being between 20 C and 37 C.

The invention may also provide a method wherein the helicoidal member first and second configurations have different pitches.

The invention may also provide a method wherein the helicoidal member has a pitch that varies between the helicoidal member proximal and distal ends.

The invention may also provide a method wherein the pitch is larger at the helicoidal member distal end than at the helicoidal member proximal end.

The invention may also provide a method wherein the guide is inserted in a deformable sleeve, the sleeve being partially inserted in the suction apertures.

In yet another broad aspect, the invention provides a system for performing a surgical procedure in a target biological tissue using a helicoidal member, the helicoidal member defining a helicoidal member longitudinal axis and substantially longitudinally opposed helicoidal member proximal and distal ends, the target biological tissue defining a target tissue exposed surface, the system including: a substantially elongated guide positionable so as to be extending at least partially through the helicoidal member along the helicoidal member longitudinal axis, the guide defining a guide tip and a guide peripheral surface extending substantially longitudinally from the guide tip, the guide peripheral surface having a peripheral surface cooled portion; a cooling subsystem operatively coupled to the guide for selectively cooling the peripheral surface cooled portion to a temperature sufficiently low to cause adhesion between the guide and the target biological tissue; a driver, the helicoidal member being mountable to the driver at the helicoidal member proximal end, the driver being operative for selectively simultaneously rotating the helicoidal member along the helicoidal member longitudinal axis and advancing the helicoidal member along the guide in a distally oriented direction; wherein, in operation, when the cooling subsystem cools the peripheral surface cooled portion and the latter is positioned to abut against the target tissue exposed surface, the peripheral surface cooled portion adheres to the target tissue exposed surface so that the driver can operated to advance the helicoidal member along the guide while driving the helicoidal member into the target biological tissue with the peripheral surface cooled portion remaining fixed relative to the target biological tissue.

Advantageously, the present system and method use a guide that can be safely secured to tissue to penetrate so that the helicoidal member can be inserted therein at a predetermined location. The proposed instrument can also be manufactured using known methods and materials at a reasonable cost.

The present application claims priority from U.S. Provisional patent applications 62/094,151 filed 19 Dec. 2014 and 62/186,708 filed 30 Jun. 2015, the contents of which is hereby incorporated by reference in its entirety.

Other objects, advantages and features of the present invention will become more apparent upon reading of the following non-restrictive description of preferred embodiments thereof, given by way of example only with reference to the accompanying drawings.

BRIEF DESCRIPTION FOR DRAWINGS

Figure 2:
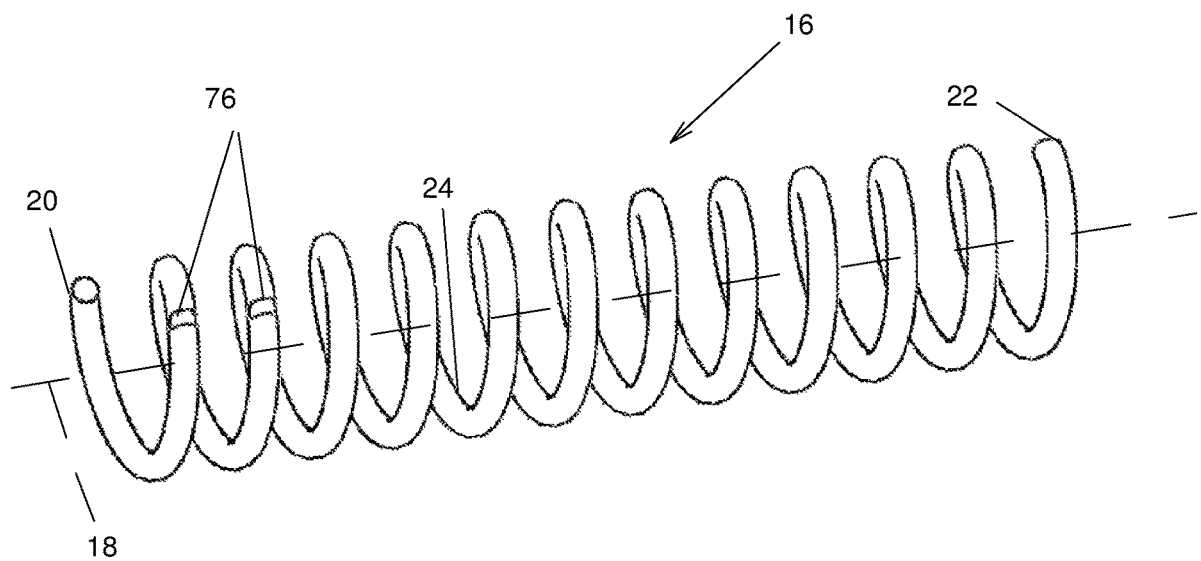
Figure 3:
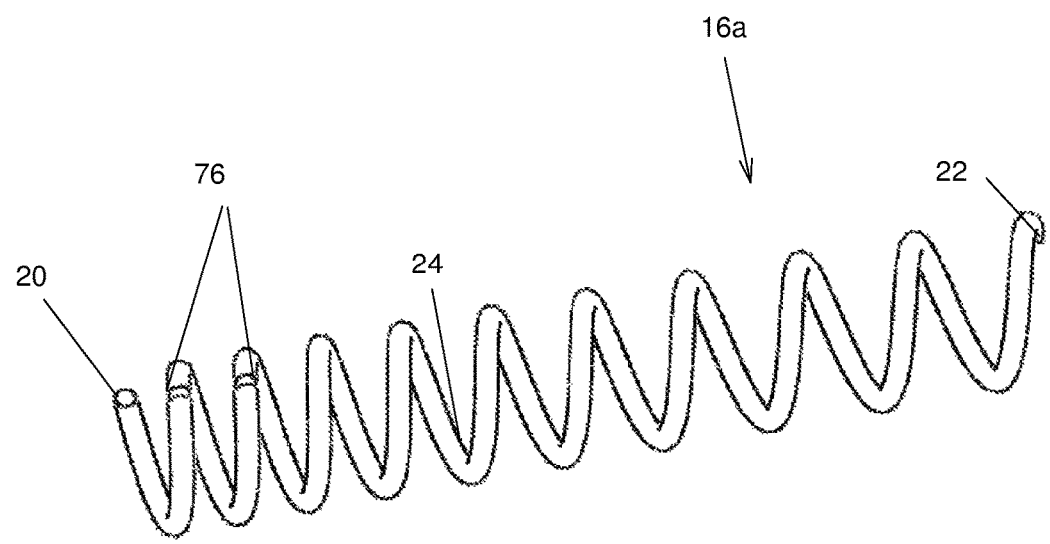
Figure 7:
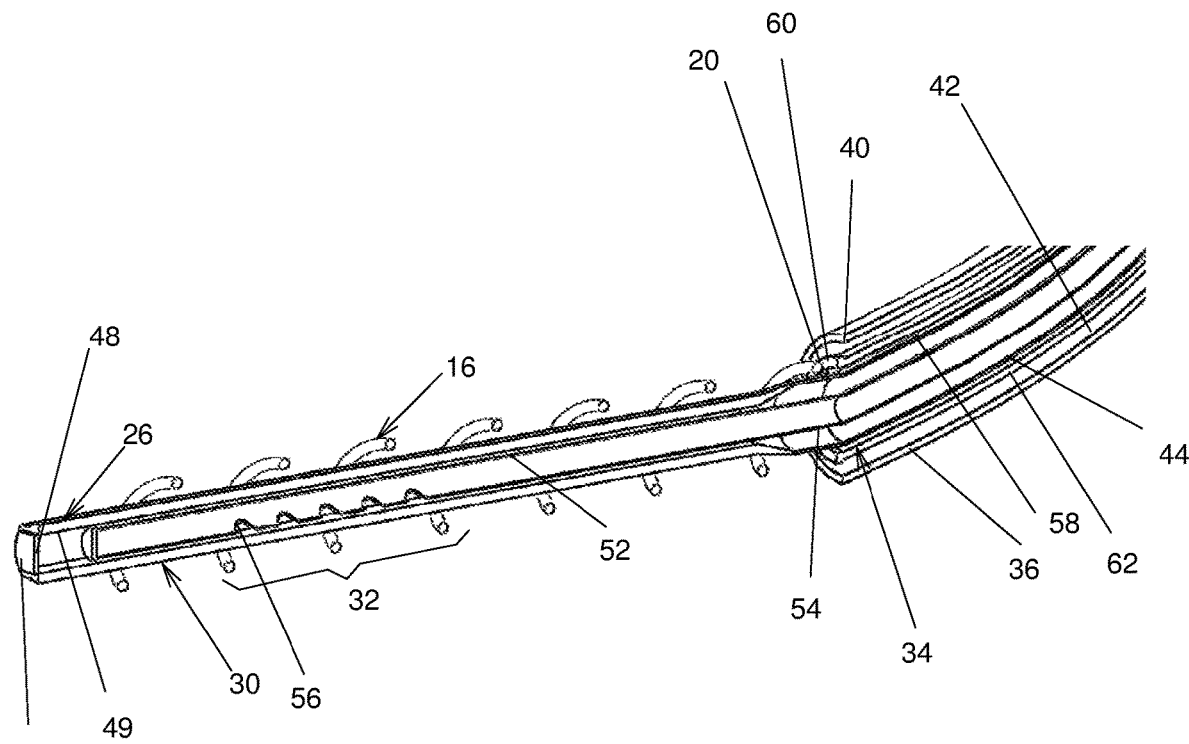

In the appended drawings:

FIG. 1, in a perspective view, illustrates a system in accordance with an embodiment of the present invention;

FIG. 2, in a perspective view, illustrates a helicoidal member part of the system shown in FIG. 1;

FIG. 3, in a perspective view, illustrates an alternative helicoidal member usable in the system shown in FIG. 1;

FIG. 4A, in a perspective view, illustrates an alternative guide usable in the system shown in FIG. 1;

FIG. 4B, in a transversal cross-sectional view, illustrates the guide shown in FIG. 4A FIG. 5A, in a perspective view, illustrates another alternative guide usable in the system shown in FIG. 1;

FIG. 5B, in a transversal cross-sectional view, illustrates the guide shown in FIG. 5A;

FIG. 6A, in a perspective view, illustrates yet another alternative guide usable in the system shown in FIG. 1;

FIG. 6B, in a transversal cross-sectional view, illustrates the guide shown in FIG. 6A;

FIG. 7, in a cut away perspective view, illustrates the guide part of the system shown in FIG. 1.

Figure 8:
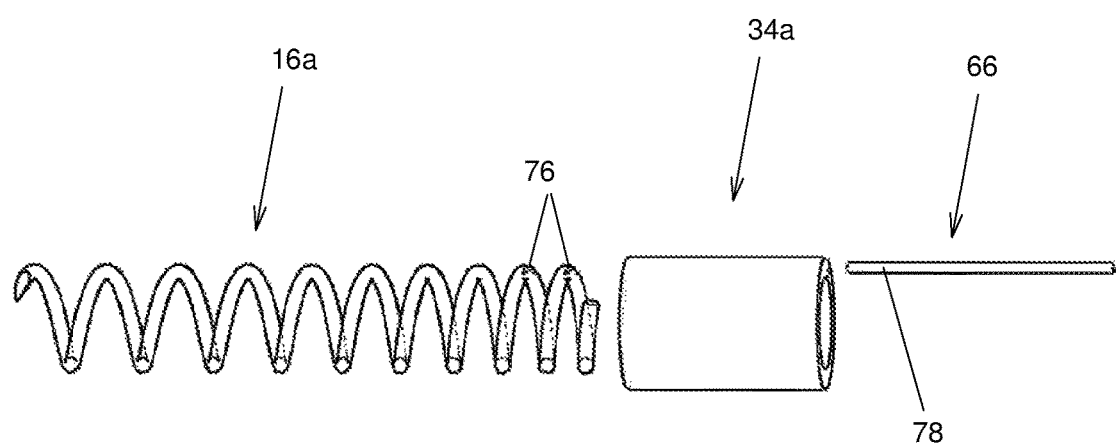
Figure 9A:
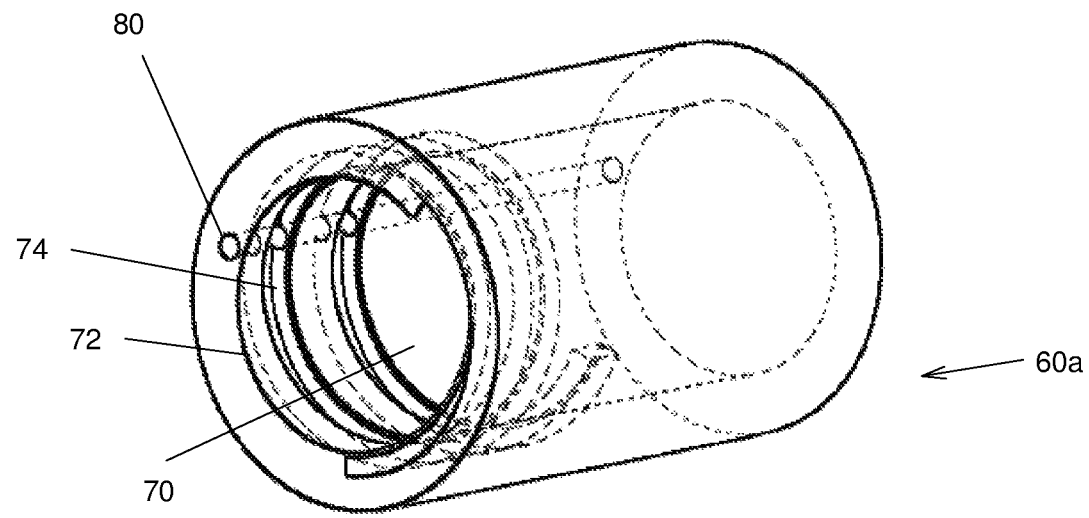
Figure 10:
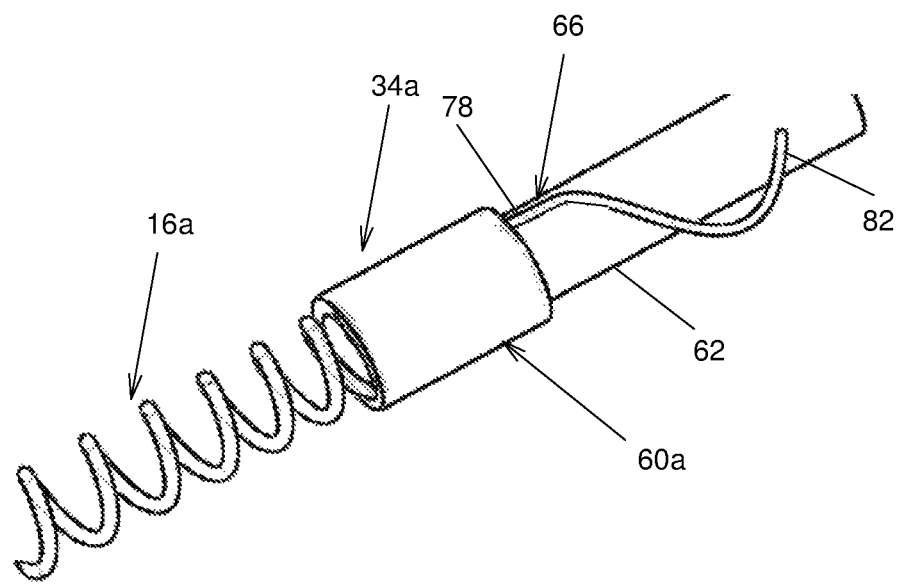
Figure 9B:
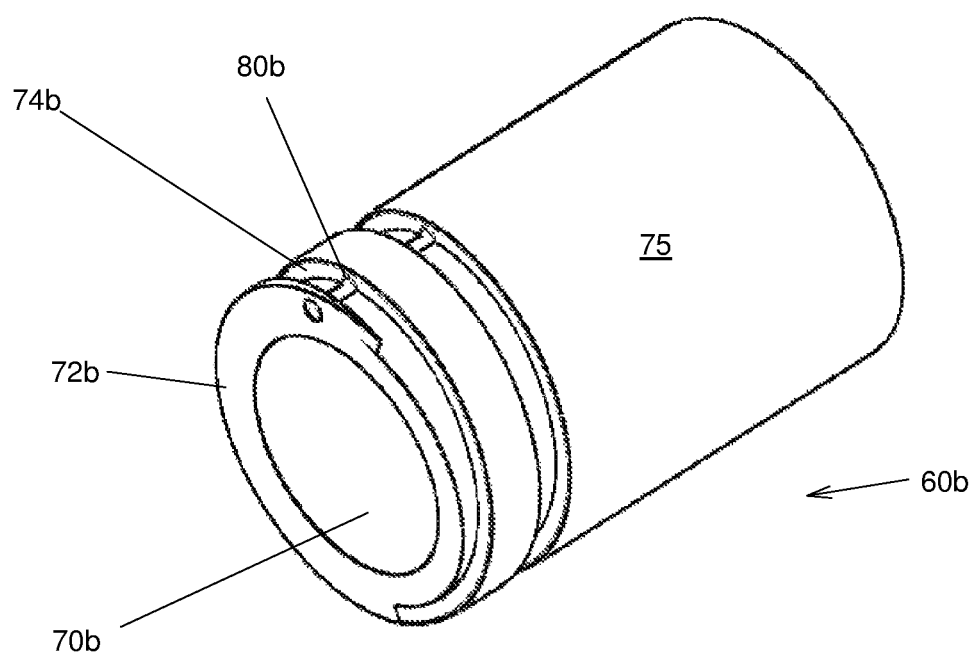
Figure 9C:
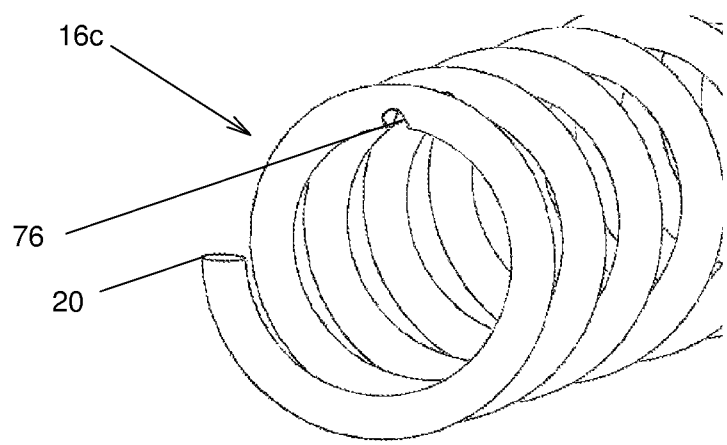
Figure 11:
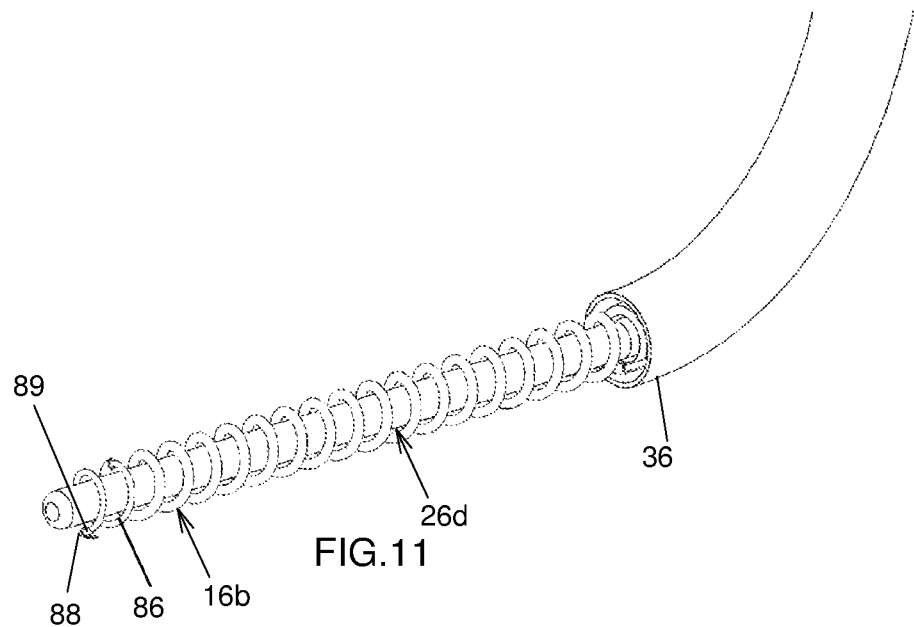
Figure 12:
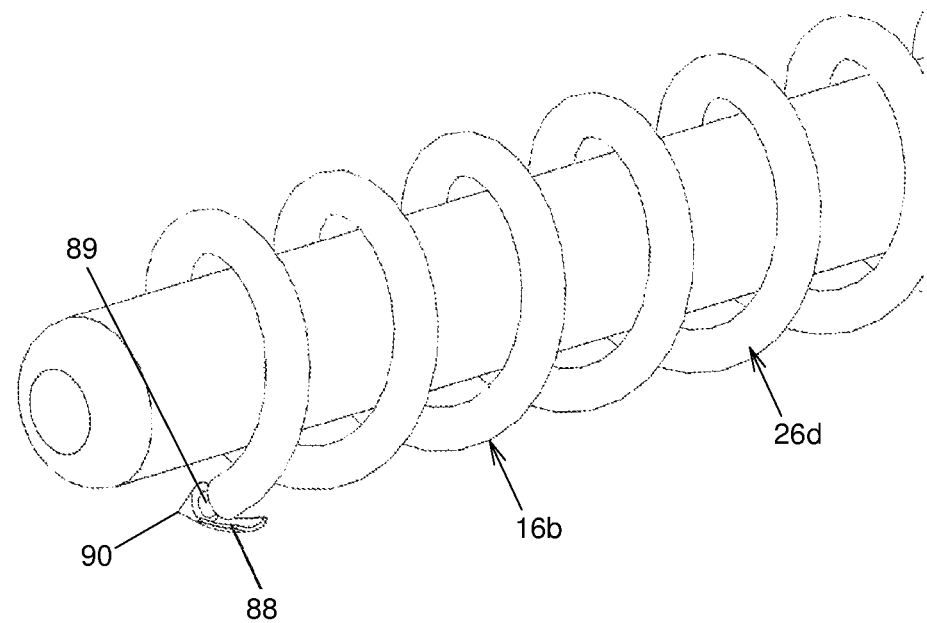
Figure 13:
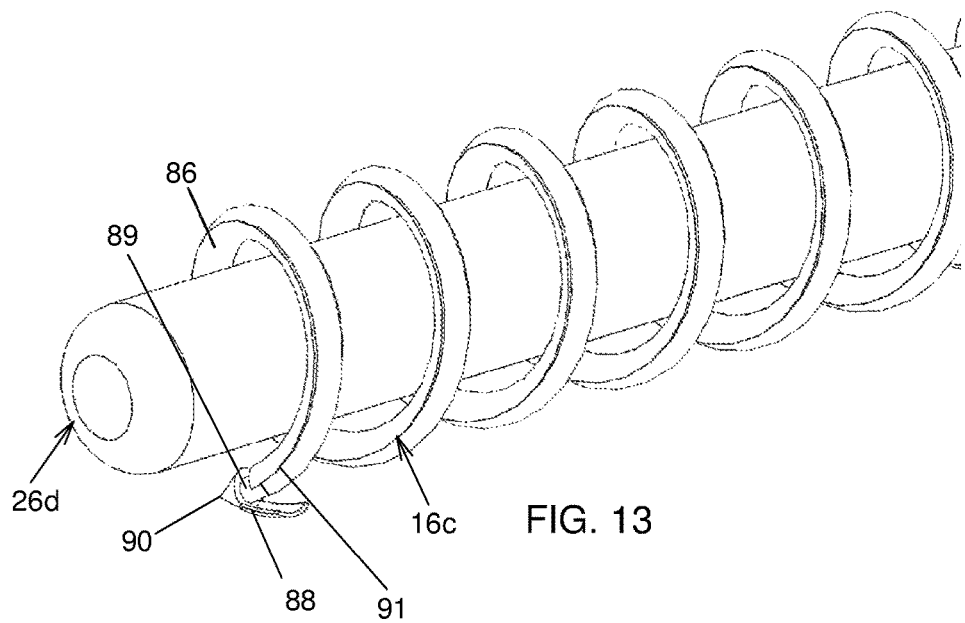
Figure 14:
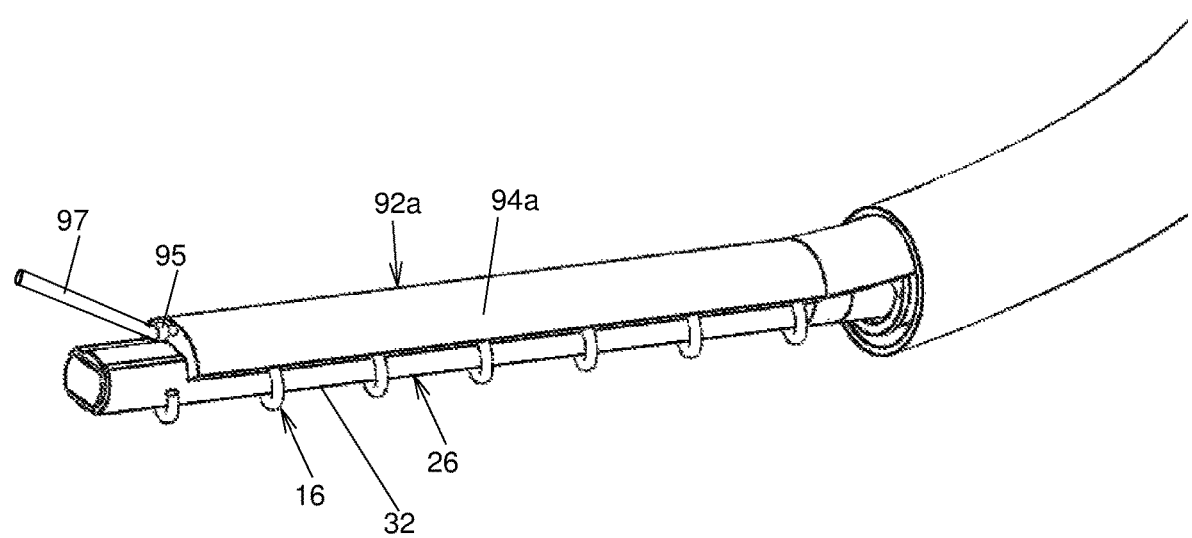
Figure 20:
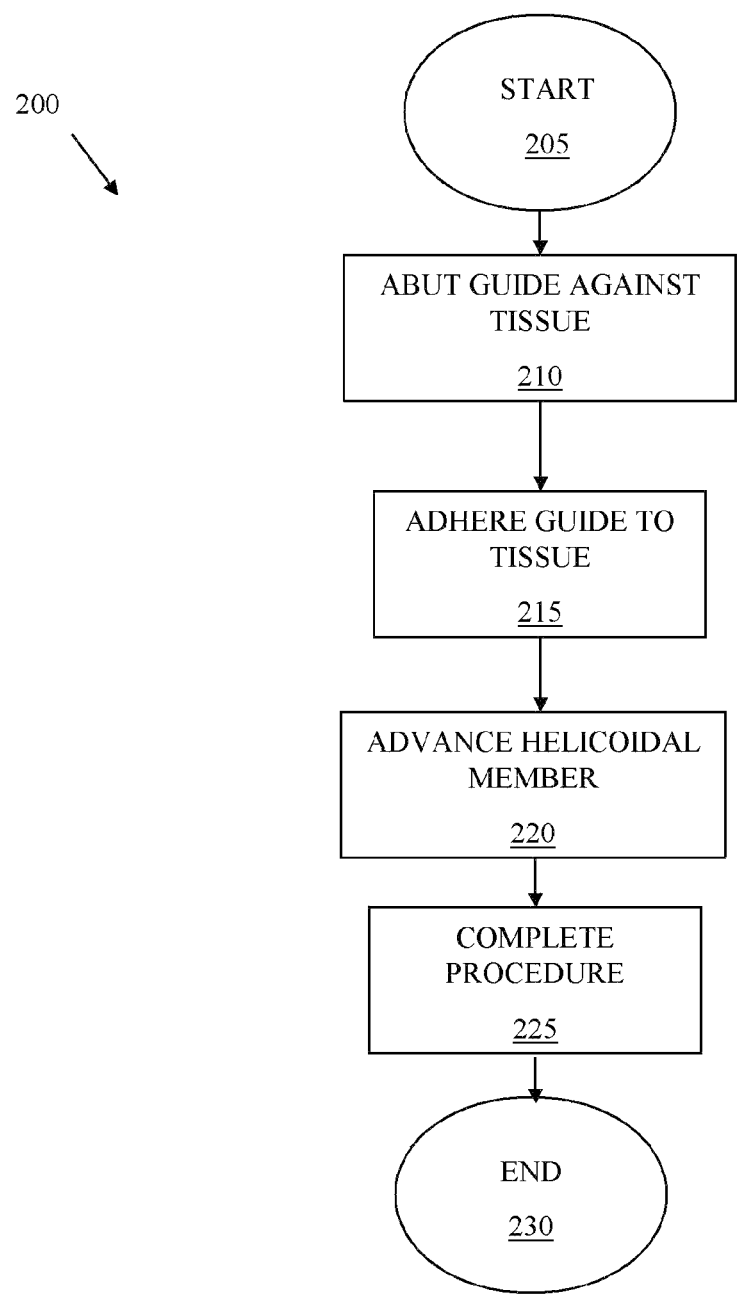
Figure 21A:
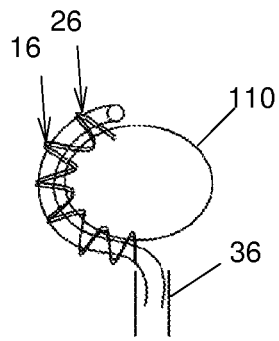
Figure 21B:
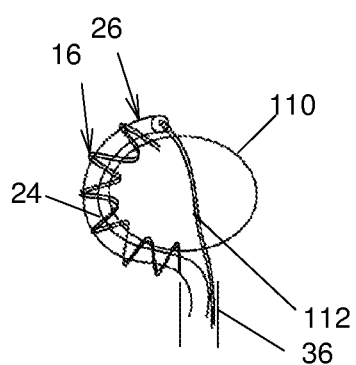
Figure 21C:
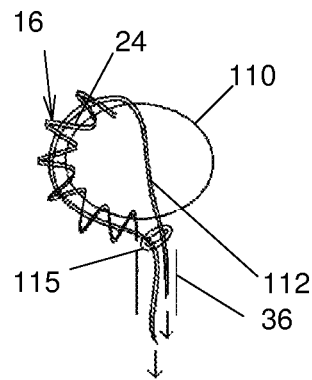
Figure 21D:
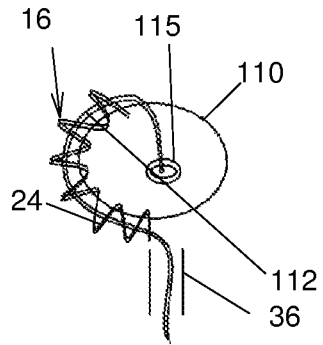
Figure 21E:
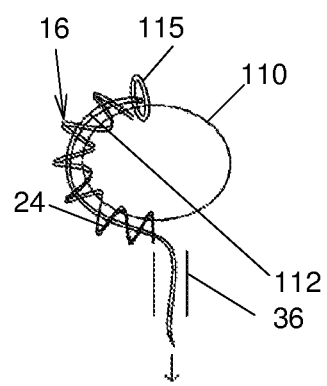
Figure 21F:
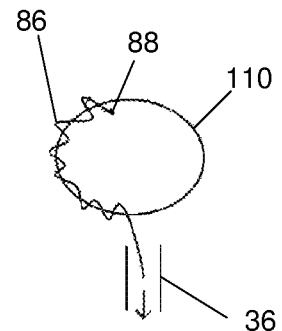
Figure 22A:
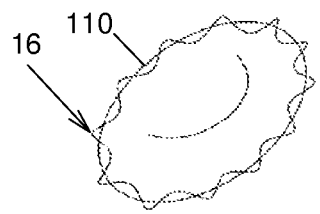
Figure 22B:
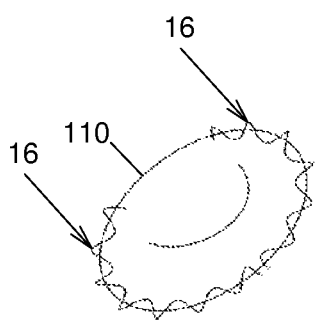
Figure 22C:
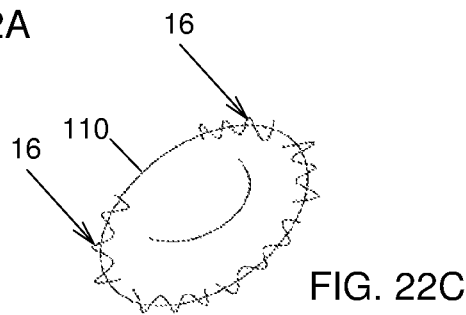
Figure 26:
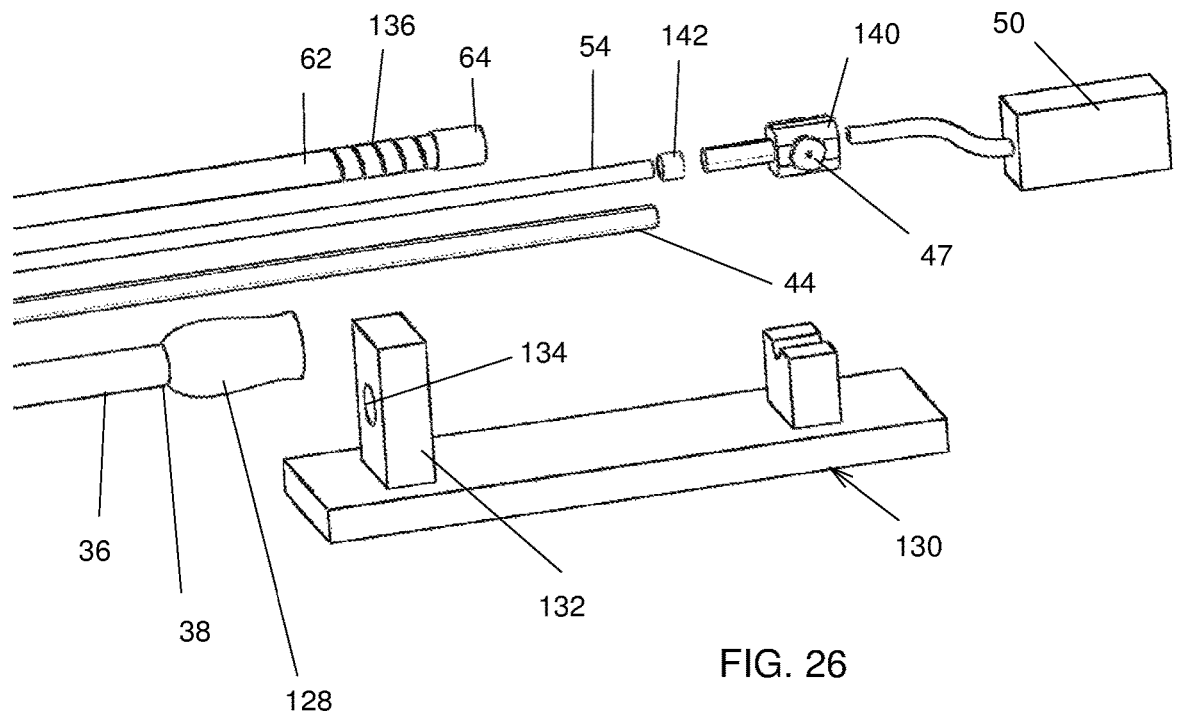
Figure 27:
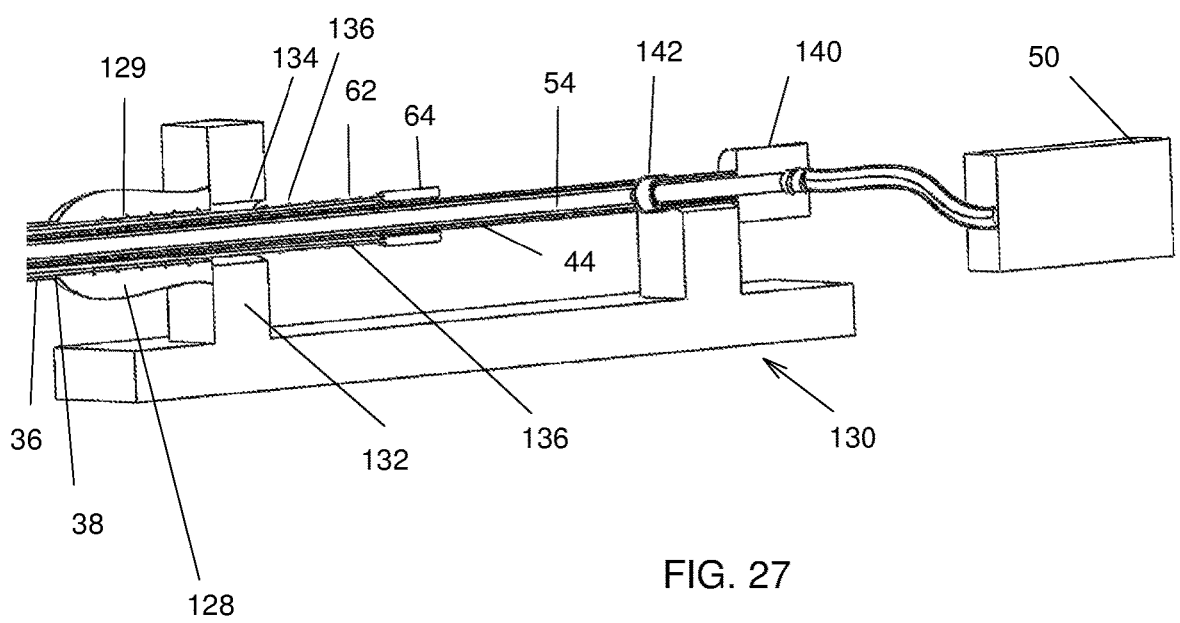

FIG. 8, in a perspective view, illustrates an attachment and an helicoidal member both usable in the system of FIG. 1, the helicoidal member being detached from the attachment;

FIG. 9A, in a perspective view, illustrates the attachment of FIG. 8;

FIG. 9B, in a perspective view, illustrates an alternative attachment;

FIG. 9C, in a perspective view, illustrate an alternative helicoidal member usable with the attachment of FIG. 9B FIG. 10, in a perspective view, illustrates the attachment and helicoidal member of FIG. 8 attached to each other;

FIG. 11, in a perspective view, illustrates yet another alternative guide and yet another alternative helicoidal member usable in the system of FIG. 1;

FIG. 12, in a perspective partial view, illustrates the guide and helicoidal member of FIG. 11;

FIG. 13, in a perspective view, illustrates yet another another alternative helicoidal member usable in the system of FIG. 1;

FIG. 14, in a perspective view, illustrates the guide of the system of FIG. 1 with an insert engaged by the helicoidal member;

FIG. 15A, in a side elevation view, illustrates an alternative insert mountable to a guide;

FIG. 15B, in a front partial cross-sectional view, illustrates the insert of FIG. 15A mounted to a guide;

FIG. 16A, in a side elevation view, illustrates an other alternative insert mountable to a guide;

FIG. 16B, in a front partial cross-sectional view, illustrates the insert of FIG. 16A mounted to a guide;

FIG. 17A, in a side elevation view, illustrates yet an other alternative insert mountable to a guide;

FIG. 17B, in a front partial cross-sectional view, illustrates the insert of FIG. 17A mounted to a guide;

FIG. 18A, in a perspective view, illustrates yet another alternative guide usable in a system similar to the system of FIG. 1, the present guide using suction to adhere to tissue;

FIG. 18B, in a schematic view, illustrate a configuration of suction apertures usable in the guide of FIG. 18A;

FIG. 18C, in a schematic view, illustrate another configuration of suction apertures usable in the guide of FIG. 18A;

FIG. 18D, in a schematic view, illustrate yet another configuration of suction apertures usable in the guide of FIG. 18A;

FIG. 18E, in a schematic transversal cross-sectional view, illustrates yet another alternative guide usable in a system similar to the system of FIG. 1;

FIGS. 19A to 19H, in schematic views, illustrate various cross-sectional configuration usable in a guide similar to the guide of FIG. 18;

FIG. 20, in a flowchart, illustrates a method of using the system of FIG. 1;

FIGS. 21A to 21C, in schematic views, illustrate successive steps in an annuloplasty procedure performed using the system of FIG. 1;

FIGS. 21D to 21F, in schematic views, alternative embodiments of an annuloplasty procedure performed using the system of FIG. 1;

FIGS. 22A to 22C, in a schematic top view, illustrate various configurations of helicoidal members usable to perform the annuloplasty procedures shown in FIGS. 21A to 21F;

FIG. 23A, in a perspective schematic view, illustrates a prosthesis in the form of a valve leaflet positioned about a valve annulus;

FIG. 23B, in a perspective schematic view, illustrates the prosthesis of FIG. 23A attached to surrounding tissue with the helicoidal member of FIG. 2;

FIG. 23C, in a perspective schematic view, illustrates an alternative prosthesis attached to surrounding tissue with the helicoidal member of FIG. 2;

FIG. 23D, in a transversal cross-sectional view, illustrates the prosthesis of FIG. 23A attached to a guide usable in the system of FIG. 1;

FIGS. 23E to 23G, in schematic views, illustrate successive steps in an implantation of a tubular valve performed using a system similar to the system of FIG. 1;

FIG. 23H, in a perspective view, illustrates the tubular valve used in the procedure illustrated in FIGS. 23E to 23G;

FIGS. 24A to 24D, in a schematic side cross-sectional view, illustrate part of the annuloplasty procedure shown in FIGS. 21A to 21C;

FIG. 24E, in a schematic side cross-sectional view, illustrate an alternative positioning of a guide to perform the annuloplasty procedure shown in FIGS. 21A to 21C;

FIGS. 25A to 25H, in schematic views, illustrate successive step in a procedure in which the system 10 is used to close a gap between two tissue portions;

FIG. 26, in an exploded view with parts removed, illustrates the system of FIG. 1; and FIG. 27, in a longitudinal cross-sectional view with parts removed, illustrates the system of FIG. 1.

DETAILED DESCRIPTION

With reference to FIG. 1, there is shown a system 10 for performing a surgical procedure in a target biological tissue 12 (shown only schematically in FIG. 1). The target biological tissue 12 defines a target tissue exposed surface 14. The target tissue exposed surface 14 is either at the surface of a subject on which the surgical procedure is performed, and thus exposed to the environment, or in one of the numerous cavities or vessels present in animals, such as for example and non-limitingly, the interior of the gastro-intestinal system, the blood vessels, cardiac chambers and airways. The target tissue exposed surface 14 may also be at the junction between two adjacent tissues or tissue portions that can move relative to each other at this junction, for example within an incision in a tissue. The target tissue exposed surface 14 is thus any surface that can be accessed to insert something in the bulk of the target biological tissue 12, and is typically exposed to gases or fluids.

The system 10 includes a substantially helicoidal member 16. As better seen in FIG. 2, the helicoidal member 16 defines a helicoidal member longitudinal axis 18 and substantially longitudinally opposed helicoidal member proximal and distal ends 20 and 22. A helicoidal member passageway 24 extending longitudinally between the helicoidal member proximal and distal ends 20 and 22.

In the present document, the terminology distal and proximal refers to the location relative to an operator (not shown in the drawings) using the system 10. Distal elements are closer to the target biological tissue 12, while proximal elements are closer to the operator of the system 10. This terminology is used to facilitate the description of the system 10 and should not be used to restrict the scope of the present invention. Also, the terminology "substantially" and "about" is used to denote variations in the thus qualified terms that have no significant effect on the principle of operation of the system 10. These variations may be minor variations in design or variations due to mechanical tolerances in manufacturing and use of the system 10. These variations are to be seen with the eye of the reader skilled in the art.

Returning to FIG. 1, the system also includes a substantially elongated guide 26 positionable so as to be extending at least partially through the helicoidal member 16 along the helicoidal member longitudinal axis 18. Referring to FIG. 7, the guide 26 defines a guide tip 28 and a guide peripheral surface 30 extending substantially longitudinally from the guide tip 28. The guide peripheral surface 30 has a peripheral surface cooled portion 32 covering at least part of the guide peripheral surface 30. The peripheral surface cooled portion 32 may cover only a small part of the guide peripheral surface 30, or may include most or all of the guide peripheral surface 30.

Returning to FIG. 1, a cooling subsystem 33 is operatively coupled to the guide 26 for selectively cooling the peripheral surface cooled portion 32 to a temperature sufficiently low to cause adhesion between the guide 26 and the target biological tissue 12. As described in further details hereinbelow, cooling is for example performed using a coolant that is refrigerated and circulated in the guide 26. In alternative embodiments, the peripheral surface cooled portion 32 is in contact with a Pelletier device that cools the peripheral surface cooled portion 32. Any other suitable cooling method may also be used to cool the peripheral surface cooled portion 32, such as for example and non-limitingly, evaporative cooling of a liquid provided in the guide 26, or by phase change of a material provided in the guide 26 so that it may absorb heat from adjacent tissue.

Returning to FIG. 7, the helicoidal member 16 is mounted to a driver 34 at the helicoidal member proximal end 20. The driver 34 is operative for selectively simultaneously rotating the helicoidal member 16 along the helicoidal member longitudinal axis 18 and advancing the helicoidal member 16 along the guide 26 in a distally oriented direction. In some embodiments, the driver 34 is configured so that the helicoidal member 16 is actively advanced while rotated. In other embodiments, the driver 34 is simply free to move longitudinally and is advanced by the helicoidal member 16 as the latter advances in the target biological tissue 12 due to rotation of the helicoidal member 16.

In operation, when the cooling subsystem 33 cools the peripheral surface cooled portion 32 and the latter is positioned to abut against the target tissue exposed surface 14, the peripheral surface cooled portion 32 adheres to the target tissue exposed surface 14 so that the driver 34 can operated to advance the helicoidal member 16 along the guide 26 while driving the helicoidal member 16 into the target biological tissue 12 with the peripheral surface cooled portion 32 remaining fixed relative to the target biological tissue 12.

More specifically, the guide 26 abuts on the target tissue exposed surface 14 from the side, as opposed from abutting from the guide tip 28. The helicoidal member longitudinal axis 18 and the target tissue exposed surface 14 are substantially parallel to each other. The peripheral surface cooled portion 32 is from a substantially longitudinally extending portion of the guide 26. The peripheral surface cooled portion 32 may reach the guide tip 28 or may be spaced apart therefrom longitudinally. Due to its helicoidal shape, rotating the helicoidal member 16 causes the latter advances in the target tissue in a corkscrew-like motion. It was found that, surprisingly, cryoadhesion of the guide 26 provides sufficient adhesion in this configuration to allow driving the helicoidal member 16 into the target biological tissue 12 as described even with the relatively large forces and torques involved in advancing the helicoidal member 16.

The system 10 is particularly useful in surgical procedures that are performed away from the target biological tissue 12, for example through a laparoscopy, percutaneous or a transcatheter procedure. In this latter case, as see in FIG. 1, the system 10 also includes a substantially elongated catheter 36 defining substantially opposed catheter proximal and distal ends 38 and 40 and a catheter lumen 42 (seen in FIG. 7) extending therebetween. The guide 26 protrudes from the catheter lumen 42 at the catheter distal end 40. However, the present invention may also be used without the catheter 36 when easy access to the target biological tissue 12 exists.

The guide 26 is substantially elongated and is typically connected to a guide actuator 44. The guide actuator 44 extends along the catheter 36 in the catheter lumen 42 to the catheter proximal end 38 and is longitudinally movable therealong. The guide actuator 44 has a rigidity sufficient to be movable substantially longitudinally along the catheter 36 so that the guide 26 protrudes more or less therefrom, but is nevertheless sufficiently flexible to follow the shape of the catheter 36 inside the patient, for example around the vasculature in the case of cardiac interventions. The guide actuator 44 terminates with a guide actuator handle 46 that allows controlling the longitudinal position of the guide 26. In some embodiments, the guide actuator 44 is substantially tubular with circular transversal cross-section to allow circulation of coolant fluid therethrough, as further described hereinbelow. In some embodiments, the guide actuator 44 and the guide 26 extend integrally from each other.

The guide 26 may have any suitable transversal cross-sectional configuration. For example, the guide 26 has a substantially oval transversal cross-sectional configuration, as shown in FIG. 1. In other embodiments, as shown for guides 26a to 26c shown respectively in FIGS. 4A, 5A and 6A, the guide may have substantially, rectangular, T-shaped or D-shaped, transversal cross-sectional configurations, among other possibilities. These transversal cross-sectional configurations are better illustrated in FIGS. 4B, 5B and 6B, respectively. In yet another embodiments, shown in FIGS. 11 to 13, a guide 26d had a substantially circular transversal cross-sectional configurations. For example, D-shaped configuration of guide 26c allows a substantially flat peripheral surface cooled portion 32c, which may contact efficiently substantially flat target tissue exposed surfaces 14. Also, the T-shaped transversal cross-sectional configuration of the guide 26b allows for peripheral surface cooled portion 32b having a pair of flat portions 35 spaced apart laterally from each other with a U-shaped portion 37 extending therefrom and therebetween. The U-shaped portion 37 may be inserted in the space between two tissue portions to attach to each other with minimal or no gap therebetween, each of the flat portions 35 abutting against one of the tissue portions. The exact size and cross sectional configuration of the guides 26, 26a, 26b, 26c and 26d allow control over the depth of insertion of the helicoidal member 16.

In some embodiments, the guide 26 is substantially rigid so that it remains with a substantially constant shape while in use. This shape may be substantially rectilinear or curved, among other possibilities. In other embodiments, the guide 26 is deformable so that its shape can be adjusted (not shown in the drawings). An exemplary deformation is from a linear configuration to an arcuate configuration and is accomplished using mechanical and/or electrical devices known to those skilled in the art. In these embodiments, the guide 26 may be either entirely deformable, or may have a section thereof that is more deformable than the remainder of the guide 26. Deformation of the guide 26 may be effected for example by using a tether secured to the guide tip 28 and extending in a distally oriented direction therefrom and returning through the catheter lumen 42. In other embodiments, the tether is inserted in a separate lumen traversing the guide 26 and guide actuator 44. The tether and can be pulled onto by the intended user of the system 10 to bend the guide 26. In other embodiments, one, two or more pairs of laterally opposed cables are secured to the guide tip 28 and extend through the catheter lumen 42 to the catheter proximal end 38. Pulling on these cables allow bending of the guide 26, for example using a bending actuator 47. The guide 26 may also be deformed using any other suitable mechanism. Such mechanisms for remotely adjusting the shape of a member at the end of a catheter are known in the art and are not described in further details herein.

In yet other embodiments, when not constrained, the guide 26 achieves a shape suitable for its intended purpose. The guide 26 is however deformable passively to allow for example passage through the catheter 36 as the latter is advanced through a patient's vasculature. In other words, once deployed adjacent the target biological tissue 12, the guide 26 achieves the shape required for the specific surgical intervention practiced. However, the guide 26 may deform to allow reaching the target biological tissue, due for examples to curves in the catheter 36. An example of such a guide 26 may be substantially arc segment shape for use in valve annuloplasty. The guide 26 can be shaped by inserting pre-shaped flexible longitudinal inserts thereinto.

Referring to FIG. 7, the guide 26 is typically hollow to define a guide cavity 49 thereinto and extends from the guide actuator 44, which is also hollow typically. The guide cavity 49 is closed at the guide tip 28 by a guide end wall 48. The guide peripheral surface 30 extends from the guide end wall 48. The guide 26 is relatively highly thermally conductive at least in the peripheral wall cooled portion 32. For example, the peripheral wall cooled portion 32 is made of metal or any heat conductive material or combination of heat conductive materials that is in contact with the coolant or that is in contact with any other cooled material. In some embodiments, creating a flexible metallic guide can be made using below type constructions or using a series of metallic rings intertwined by a polymer.

The cooling subsystem 33 includes a coolant source 50 (shown in FIG. 1). The coolant source 50 is in a fluid communication relationship with a coolant passageway 52, seen in FIG. 7, for providing cooled coolant thereto. The coolant passageway has a portion thereof substantially adjacent to the peripheral surface cooled portion 32 and in a thermal transfer relationship therewith. The coolant passageway 52 is configured for circulating a coolant therethrough to cool the peripheral surface cooled portion 32.

The coolant source 50 is a conventional device that is used to cool a conventional coolant, such as the those used in cryosurgery. In some embodiments, the temperature to which the coolant is cooled is controlled so that no or only minimal irreversible damages are caused in the target biological tissue 12. In other embodiments, the target biological tissue 12 may be cooled with some damages without affecting the normal physiology of an organ including the target biological tissue 12. The coolant source 50 typically also includes a pump to circulate the coolant through the coolant passageway 52. The coolant can be a liquid or a gas or a change of phase can occur in the guide cavity 49.

In some embodiments, temperature control is made by supplying to the coolant passageway 52 coolant at a predetermined temperature. In other embodiments (not shown in the drawings), the coolant source 50 is operatively coupled to a temperature sensor, such as a thermocouple, at the peripheral surface cooled portion 32 so that the temperature of the latter can be controlled by supplying cooler or warmer coolant to the coolant passageway 52.

In some embodiments, the coolant passageway 52 is formed as follows. A coolant tube 54, which forms part of the coolant passageway 52, extends in the guide 26 along a portion thereof. The coolant tube 54 may also extends along the catheter 36 when the latter is provided. The coolant tube 54 is provided with at least one coolant tube outlet 56, and in some embodiments a series of longitudinally spaced apart coolant tube outlets 56, located in the guide 26 substantially adjacent the peripheral surface cooled portion 32. The coolant tube outlets 56 typically extend substantially radially and proximally relative to the peripheral surface cooled portion 32 so as to provide the coolant directly adjacent the peripheral surface cooled portion 32. The coolant tube 54 has at least a portion thereof that is spaced apart from the guide 26 so that coolant can be circulated from the coolant tube 54, through the coolant tube outlets 56 and between the coolant tube 54 and the guide 26. A coolant return passageway 58 is provided for collecting the coolant from the interior of the guide 26 and return it to the coolant source 50 through the catheter 36. For example, the coolant tube 54 is of an outside diameter that is slightly smaller than an inner diameter of the guide 26 so that when the coolant is forced under pressure in the coolant tube 54, the coolant can exit the coolant tube through the coolant tube outlets 56 and get to the coolant return passageway 58. In other cases the coolant tube 54 diameter is much smaller than the inner diameter of the guide 26 to allow for coolant expansion, thus triggering a decrease in temperature. In some embodiments, the coolant tube outlets 56 are substantially adjacent to the peripheral surface cooled portion 32 to provide optimal cooling of the latter. In some examples, the coolant is returned in a dedicated coolant return tube.

In alternative embodiments (not shown), the cooling subsystem 33 includes a cooling tube that reaches the interior of the guide 26 and abut against the peripheral surface cooled portion 32. The cooling tube circulates the coolant in a closed circuit between the guide 26 and the coolant source 50.

In some embodiments, the helicoidal member 16 has the same shape, or substantially the same shape, before and after insertion in the target biological tissue 12. In other words, the helicoidal member 16 does not deform substantially during insertion. In other embodiments, the helicoidal member 16 includes a shape memory material, for example Nitinol™ and changes between a helicoidal member first configuration and a helicoidal member second configuration at a transition temperature. For example, the transition temperature is between 20 C and 37 C. In some embodiments, the helicoidal member first and second configurations have different pitches. The pitch is defined in the present document as the longitudinal distance covered when advancing along the helicoidal member one full turn about the helicoidal member longitudinal axis 18.

In some embodiments, as seen in FIG. 1, the pitch of the helicoidal member 16 is constant along the whole helicoidal member 16. In other embodiments, the helicoidal member 16a has a pitch that varies between the helicoidal member proximal and distal ends 20 and 22, as seen in FIG. 3. In such embodiments, the pitch may be larger at the helicoidal member distal end 22 than at the helicoidal member proximal end 20. This configuration provides a compression of the target biological tissue 12 as the helicoidal member 16 is advanced thereinto. The helicoidal member distal end 22 sharpness is varied depending on target biological tissue 12 properties.

The helicoidal member 16 may be metallic. The helicoidal member 16 may be biodegradable. Also, in some embodiments, the helicoidal member 16 may be provided with small tins on its surface or finishing that increases the friction with surrounding target biological tissue 12.

As seen for example in FIG. 7, the driver 34 includes an attachment 60 for holding the helicoidal member 16, a driver actuator 62 for selectively rotating the driver 34. The driver actuator 62 terminates typically with a driver handle 64 opposed to the attachment 60. When the catheter 36 is present, the driver actuator 62 extends thereinto with the driver handle 64 protruding therefrom. For example, the driver actuator 62 includes is a substantially elongated tube through which the guide 26 and part of the guide actuator 44 are inserted. The attachment 60 and guide actuator 62 may extend integrally from each other or be two separate components permanently or reversibly secured to each other. The guide 26/guide actuator 44 assembly and the driver actuator 62 are longitudinally movable relative to each other. In some embodiments, the driver actuator 62 includes a braided or coiled catheter to allow good torque transfer to the helicoidal member 16.

In some embodiments, as shown in FIG. 1, the helicoidal member 16 is permanently secured to the driver 34, for example by extending integrally therefrom. In other embodiments, as seen in FIGS. 8 to 10, the helicoidal member 16 is selectively detachable from the driver 34a. A specific embodiment of this latter case is further described in the following paragraphs.

In this embodiment, the driver 34a includes a driver lock 66 movable between a locked configuration (seen in FIG. 10) and an unlocked configuration (seen in FIG. 8 with the helicoidal member 16 detached from the driver 34a). In the locked configuration, the helicoidal member 16 is locked to the driver 34a. In the unlocked configuration, the helicoidal member 16 is detachable from the driver 34a.

For example, as better seen in FIG. 9A, the attachment 60a defines an attachment passageway 70 opened distally at an attachment passageway distal end 72. A substantially helicoidal thread 74 extends into the attachment passageway 70 from attachment passageway distal end 72. The helicoidal thread 74 is configured and sized for receiving part of the helicoidal member 16 or 16a (not shown in FIG. 9A) at the helicoidal member proximal end 20. For example, the helicoidal thread 74 has a configuration complementary to that of the helicoidal member 16 or 16a at the helicoidal member proximal end 20 to substantially snugly hold the helicoidal member 16 in the attachment passageway 70.

The driver lock 66 can be any suitable lock that can prevent detachment of the helicoidal member 16 from the attachment 60a. In some embodiments the helicoidal member 16 or 16a is provided with at least one notch 76 (better seen in FIG. 3) substantially longitudinally extending substantially adjacent the helicoidal member proximal end 20 and the driver lock includes a pin (or rigid wire) 78 (seen in FIGS. 8 an 10) insertable in the notch 76 when the helicoidal member 16 is operatively secured to the driver 34 in the helicoidal thread 74. The pin 78 is selectively removable from the notch 76. Removal of the pin 78 from the notch 76 unlocks the helicoidal member 16, which can then be removed by rotating the attachment 34a and helicoidal member 16 relative to each other.

There may be more than one notch 76 provided, all longitudinally aligned along the helicoidal member 16. For example, the notches 76 are provided at the periphery of the helicoidal member 16 and a substantially rectilinear and substantially longitudinally extending pin receiving passageway 80 may extend in the attachment 60a, as seen in FIG. 9A. The pin receiving passageway 80 receives the pin 78 thereinto and intersects the helicoidal thread 74 in register with the position of the notches 76 when the helicoidal member 16 is operatively secured to the attachment 60. The pin 78 is longitudinally movable along the pin receiving passageway 80.

Removal of the pin 80 from the pin receiving passageway 78 may be performed in any suitable manner. For example, a wire 82 (seen in FIG. 10) is secured to the pin 80 and extends in the catheter 36. The pin 80 is removable from the pin receiving passageway 78 by pulling on the wire 82.

In another embodiment, as seen in FIG. 9B, the attachment 60b is substantially tubular with circular cross-sectional configuration and defines an attachment passageway 70b opened distally through which the guide 26 (not seen in FIG. 9A) can pass. A substantially helicoidal thread 74b is formed on the outer peripheral surface 75 of the attachment 60b and extends from the attachment distal end 72b. The helicoidal thread 74b is configured and sized for receiving part of an alternative helicoidal member 16c (seen in FIG. 9C) at the helicoidal member proximal end 20. The helicoidal member 16c is similar to the helicoidal member 16, except that the notches 76 face inwardly. For example, the helicoidal thread 74b has a configuration complementary to that of the helicoidal member 16c at the helicoidal member proximal end 20 to substantially snugly hold the helicoidal member 16c. A pin 78 (not shown in FIG. 9B) is insertable in a pin receiving passageway 80b that intersects the helicoidal thread 74b and locks the helicoidal member 16c to the attachment 60b, similarly to the manner in which the helicoidal member 16 is locked to the attachment 60a.

FIGS. 26 and 27 better illustrate various features of the system 10 at the proximal end thereof. In some embodiments, a catheter end piece 128 receives the catheter 36 at the catheter proximal end 38. The catheter end piece 128 defines an end piece passageway 129 (seen in FIG. 27) that is in prolongation of the catheter lumen 42. The end piece passageway 129 is threaded internally. The catheter end piece 128 is mountable to a base 130 in any suitable manner. The base 130 defines an end piece mount 132 for removably mounting the catheter end piece 128 thereto. The end piece mount 132 defines a mount aperture 134 extending therethrough in register with the end piece passageway 129.

The driver actuator 62 is substantially tubular and provided with external threads 136 configured for engaging the threads of the end piece passageway 129 and is long enough to protrude from the catheter end piece 128 and end piece mount 132 when inserted in the catheter 36. Rotating the driver actuator 62 thus advances or retracts the driver actuator 62 along the catheter 36 over the guide actuator 44.

When the system 10 is assembled, the coolant tube 54 is inserted in the guide actuator 44, which itself is inserted in the driver actuator 62, which itself is inserted in the catheter 36. Those components typically have a generally cylindrical configuration and in embodiments in which it is required, are flexible so as to allow bending of the catheter 36 and components contained therein. The coolant source 50 is coupled to the coolant tube 54 and guide actuator 44 through a coupler 140, which may support the bending actuator 47 when the latter is present. The coupler 140 is typically easily releasable from the coolant tube 54 and the guide actuator 44 through a quick release coupler 142. This allows easy removal of the driver actuator 62 to insert different helicoidal members 16 during a surgical procedure. The coupler 140 is also configured to suitably convey the coolant returning between the coolant tube 54 and guide actuator 44 to the coolant source 50 and convey the cold coolant coming from the latter to the coolant tube 54.

Referring to FIG. 11, in some embodiments a hook 88 is removably mountable to the helicoidal member 16b. A suture thread 86 is secured to the hook 88. For example the hook 88 is crimped to the end of the suture thread 86. In other embodiments (not shown in the drawings), the hook 88 defines a suture eye and a suture thread 86 is attachable to the suture eye. In some embodiments, the helicoidal member 16b is made of a hollow tube and the suture thread 86 extends through the helicoidal member 16b. The hook 88 has a part thereof insertable in the hollow tube at the helicoidal member distal end 22. For example, a hook attachment 89 part of the hook 88 is configured to be slidably inserted in the helicoidal member 16b. The hook 88 is typically terminated by a sharp point 90, as better seen in FIG. 12. In other embodiments, the helicoidal member 16c, seen in FIG. 13, defines a helicoidal groove 91 therealong receiving the suture thread 86.

The hook 88 is configured so that the helicoidal member 16b may be advanced relatively easily in the target biological tissue 12 with the hook 88 remaining secured to the helicoidal member 16b. The hook 88 is also configured so that withdrawing the helicoidal member 16b from the target biological tissue 12 causes the latter to catch the hook 88 so that the hook 88 is detached from the helicoidal member 16b or 16c as the target biological tissue 12 pulls on the hook 88. In these embodiments, the driver 34 is further operative for retracting the helicoidal member 16b in a proximally oriented direction.

In some embodiments, the system 10 further includes an insert. Four different inserts 92a, 92b, 92c and 92d are shown in FIGS. 14, 15A and B, 16A and B and 17A and B respectively. However, any other suitable insert is usable. The inserts 92a, 92b, 92c and 92d are elements that are mountable to the guide 26 and engaged by the helicoidal member 16. The inserts 92a, 92b, 92c and 92d and the guide 26 are longitudinally movable relative to each other. The inserts 92a, 92b, 92c and 92d are elements that are delivered along with the helicoidal member 16 so that when the helicoidal member 16 remains in the target biological tissue 12, the helicoidal member 16 engages the insert 92a, 92b, 92c and 92d, which is thus attached at the target tissue exposed surface 14 after the helicoidal member 16 has been delivered and detached from the driver 34. Such inserts 92a, 92b, 92c and 92d may be used to secure a prosthesis to the target biological tissue 12 or simply to provide a smoother interface and/or biocompatibility between the helicoidal member 16 an adjacent lumen or cavity. Smoothening is advantageous for example in blood vessels or in the heart as this will reduce turbulence around the helicoidal member 16. This smooth insert outer line would also promote endothelial cells build up. In other embodiments, the insert 92a, 92b, 92c and 92d may be used to deliver a drug or cells at the target biological tissue 12. The insert 92a, 92b, 92c and 92d can then have the drug or cells embedded therein and be permeable to the drug or be bioresorbable. Such inserts 92a, 92b, 92c and 92d may facilitate permanent implantation of the helicoidal member 16 in the target biological tissue 12 by promoting healing and/or tissue growth.

Referring to FIG. 14, the insert 92a includes a substantially resiliently deformable piece of material 94a provided opposed to the peripheral surface cooled portion 32 and extending along the guide 26. For example, the insert 92a is made of a foam and may have a length that is larger than that of the helicoidal member 16, as seen in FIG. 14, or that is similar or shorter to that of the helicoidal member 16 (not shown in the drawings). The insert 92a has a shape that allows snugly fitting to the guide 26 and the helicoidal member 16 is inserted through the insert 92a. Rotation of the insert 92a about the longitudinal axis of the guide 26 is prevented by the non-cylindrical shape of the guide 26. In some embodiments, the insert 92a is slightly compressed when mounted on the guide 26 to further prevent such rotation or the insert 92a can be secured to guide 26 with adhesive and is dislodged by force after the helicoidal member 16 penetrates the sleeve insert 92a. Thus, in some embodiments, the guide 26 with insert 92a secured thereto are first positioned, without the helicoidal member 16 engaging the insert 92a, and then the helicoidal member 16 is advanced, thus engaging the the insert 92a.

In some embodiments, a distally provided tether attachment 95 is provided for attaching a tether 97 to the insert 92a. In other embodiments, the tether 97 extends integrally from the insert 92a.

Referring to FIG. 15A, the insert 92b includes a substantially tubular membrane 94b positioned over the guide peripheral surface 30. The membrane 94b is provided with apertures 96 in register with the peripheral surface cooled portion 32 of the guide 26e to allow adhesion. The guide 26e is similar to the guide 26, but includes a substantially flat peripheral surface cooled portion 32 The membrane 94b is typically longer than the helicoidal member 16. In some embodiments, the insert 94b is provided with a body 99b made of a substantially resiliently deformable material, as seen in FIG. 15B that can be engaged by the helicoidal member 16 (not shown in FIG. 15B).

Another type of insert 92c is shown in FIGS. 16A and 16B. As seen in FIG. 16B, the guide 26f usable with the insert 92c defines a pair of substantially longitudinally extending mounting grooves 100, opposed to the peripheral surface cooled portion 32. The insert 92c defines a pair of substantially longitudinally extending mounting rods 102 each mounted in a respective one of the mounting grooves 100, thus securing the insert 92c to the guide 26f. The insert 92c can be also engaged by the helicoidal member 16.

FIGS. 17A and 17B illustrate the insert 92d. As seen in FIG. 17B, the insert 92d includes a membrane 94d positionable opposed to the peripheral surface cooled portion 32 and through which the helicoidal member 16 (not shown in FIG. 17B) can be inserted. The insert 92d includes attachment loops 98 securing the membrane 94d to the guide 26e, the attachment loops 98 extending circumferentially around the guide 26e at longitudinally spaced apart positions therealong.

FIG. 18A illustrates an alternative guide 106. The guide 106 is similar to the guide 26, except that adhesion with the target tissue exposed surface 14 is made though suction. As such, in a system including the guide 106, the cooling subsystem 33 is omitted and the guide 106 is hollow and provided with radially extending suction apertures 108. The guide 106 may be connected to a conventional suction apparatus 113 so that suction can be selectively exerted through the suction apertures 108. Such suction adheres the portion of the guide adjacent the suction apertures 108 to any surface adjacent thereto. In other embodiments, a suction apparatus is not provided. Instead, each suction aperture 108 leads to an enclosed deformable cavity. Deforming the cavity to increase its volume then provides suction.

The guide 106 and suction apertures 108 can have various configurations. For example, a guide 106a including a series of longitudinally spaced apart suction apertures 108a having a substantially ellipsoidal shape is shown schematically in FIG. 18B. A guide 106b including a series of longitudinally spaced apart suction apertures 108a having a substantially rectangular shape is shown schematically in FIG. 18B. A guide 106c including an array of spaced apart suction apertures 108c having a substantially circular shape is shown schematically in FIG. 18D.

The transversal cross-sectional configuration of the guide 106 can also have various shapes. The guide 26 may also be replaced by guides having such transversal configurations. FIGS. 19A to 19H illustrate schematically such transversal cross-sectional configurations. The suction surface 109 is the surface of the guide 106 through which the suction apertures 108 extend. FIG. 19A illustrates a guide 106d having a substantially trapezoidal suction surface 109d. FIG. 19B illustrates a guide 106e having a substantially T-shaped suction surface 109e. FIG. 19C illustrates a guide 106f having a substantially flat suction surface 109f, the guide 106f having a substantially rectangular transversal cross-sectional configuration. FIGS. 19D and 19E illustrate respectively guides 106g and 106h having a substantially flat suction surfaces 109g and 109h, the guides 106g and 106h having a transversal cross-sectional configuration corresponding to a portion of a disc. FIG. 19F illustrates a guide 106i having a substantially arc segment shaped suction surface 109i, the guide 106i having a substantially circular transversal cross-sectional configuration. The guide 106j of FIG. 19 includes two elements. The larger element, with a generally half-moon shaped transversal cross-sectional configuration may be structural and support a smaller element of similar configuration, but flipped so as to define an arc segment shaped suction surface 106j. FIG. 19H illustrates a guide 106k having a substantially arc segment shaped and convex suction surface 109k, the guide 106k having a transversal cross-sectional configuration corresponding to a portion of a disc. Other shapes for the guide 106 are also within the scope of the invention.

FIG. 18E illustrates another embodiment of a guide 106a using suction to adhere to the tissue exposed surface 14. The guide 106a is hollow and provided with the suction apertures 108. The guide 106a is in communication with a suction apparatus 113 (not shown in FIG. 18E, as in the guide 106. A sleeve 111 covers the guide 106a. The sleeve 111 is deformable and at least partially inserted in the suction apertures 108. The sleeve 111 may be sealed around the guide 106a, or only sealed at the edge of each suction aperture 108. The sleeve 111 prevents biological material from entering the guide 26g. When the sleeve 111 is completely sealed around the guide 106a, sterilization of the guide 106a is also facilitated.

The system 10 is usable in many surgical procedures. For example, the system 10 is usable to maintain in contact two sides of an incision to promote healing of the incision. To that effect, the helicoidal member 16 may be inserted so that it intersects both sides of the incision and is then left in the target biological tissue 12 after being detached from the driver 34. In other embodiments, the helicoidal member 16b is used to thread the suture thread 86 between the two sides of the incision and is then withdrawn with the hook 88 remaining anchored in the target biological tissue 12. After withdrawal, one can pull on the suture thread to close the incision. In another example, the system 10 is also usable in any procedure in which an anchor similar to the helicoidal member 16 is to be implanted. Such procedures include implantation of the anchor alone in the target biological tissue 12, or to anchor a prosthesis to the target biological tissue 12, such as a cardiac valve. The system 10 is for example usable to implant the helicoidal member 16 in an annuloplasty procedure or to implant a replacement cardiac valve.

Generally speaking, referring to FIG. 20, the invention provides a surgical method 200 using one of the guides 26, 26a, 26b, 26c, 26d, 26e or 26f or 106, or any other suitable guide, to assist in insertion of one of the helicoidal members 16, 16a or 16b in a target biological tissue 12. For ease of reference and to improve readability, the method 200 will be described with reference to the helicoical member 16 and guide 26 only, with the understanding that other guides, described or not in the present application, and other helicoidal members, described or not in the present application, may be used. The method 200 starts at step 205 and includes step 210 of abutting a substantially longitudinally extending portion of the guide 26 against the target tissue exposed surface 14 with the helicoidal member 16 mounted thereto so that at least a portion of the guide 26 is inserted in the helicoidal member passageway 24 substantially parallel to the helicoidal member longitudinal axis 18. The method 200 also includes step 215 of adhering the substantially longitudinally extending portion of the guide 26 to the target tissue exposed surface 14 and step 220 of advancing the helicoidal member 16 in the target biological tissue 12 in a substantially helicoidal movement with the guide 26 remaining substantially fixed relative to the target biological tissue 12. Finally the method 200 also includes in some embodiments step 225 of completing the procedure and ends at step 230.

Step 225 depends on the exact surgical procedure performed. In some embodiments, step 225 includes detaching the helicoidal member 16 from the driver 34 so that the former remains implanted in the target biological tissue 12 and detaching the guide 26 from the target tissue exposed surface 14 with the helicoidal member 16 remaining in the target biological tissue 12. In some embodiments, step 225 also includes delivering the insert 92a, 92b, 92c or 92d while advancing the helicoidal member 16 so that when the helicoidal member 16 remains in the target biological tissue 12, the insert 92a, 92b, 92c or 92d engaging the helicoidal member 16 to be secured to the target biological tissue 12.

In other embodiments, step 225 includes withdrawing the helicoidal member 16b from the target biological tissue 12 so that the hook 88 hooks the target biological tissue 12 and the suture thread 86 remains in the target biological tissue 12. In these embodiments, the helicoidal member 16b is used to insert the suture thread 86 in a helicoidal configuration in the target biological tissue 12. Step 225 may then also include pulling on the suture thread 86 to tighten the suture thread 86. This action may compress parts of the target biological tissue 12. This action may also bring together two sides of an incision or other opening in the target biological tissue 12.

Step 210 may include many actions. For example, in the case of transcatheter procedures, step 210 includes positioning the catheter 36 in a conventional manner at a location suitable to perform the transcatheter procedure and then inserting the guide 26 with the helicoidal member 16 positioned at least partially thereonto through the catheter 36 so that the guide 26 is adjacent to the target tissue exposed surface 14, at a predetermined location. Then, the catheter 36 can be moved to cause contact between the target tissue exposed surface 14 and the guide 26. This procedure can be guided in a conventional manner, for example through 3D echocardiography and fluoroscopy. In some embodiments, the guide 26 may be provided with a sensor, such as a force sensor or electrical sensor, among other possibilities to detect contact with the target tissue exposed surface 14. In some embodiments, step 210 also includes adjusting the shape of the guide 26 before adhering the substantially longitudinally extending portion of the guide 26 to the target tissue exposed surface 14.

In some embodiments, the guide 26 is used for cryoadhesion. In this method, adhering the substantially longitudinally extending portion of the guide 26 to the target tissue exposed surface 14 includes cooling at least part of the guide 26 to a predetermined temperature, using the cooling subsystem 33. The predetermined temperature is low enough to cause cryoadhesion between the substantially longitudinally extending portion of the guide 26, in this case part of the peripheral surface cooled portion 32, and the target tissue exposed surface 14. In some embodiments, the predetermined temperature is low enough to allow cryoadhesion, but remains high enough and is applied for a duration short enough that substantially no irreversible physiological damages are caused to the target biological tissue 12. In other embodiments, some irreversible physiological damages may be caused to the target biological tissue 12. For example the predetermined temperature is between 0 and −40° C., or between −20 and −40° C.

Depending on the procedure to perform, the helicoidal member 16 may be distally located relative to the longitudinally extending portion of the guide 26, proximally located relative to the longitudinally extending portion of the guide 26 or at least partially in register with the longitudinally extending portion of the guide 26. In some embodiments, the helicoidal member 16, 16a or 16b and guide 26 have substantially similar lengths and are substantially in register with each other.

In other embodiments, the guide 106 is used and adhering the substantially longitudinally extending portion of the guide 106 to the target tissue exposed surface 14 includes exerting a suction through the suction apertures 108, thus abutting the suction surface 109 against the target tissue exposed surface 109. In yet other embodiments, a guide similar to the guide 106 is used to inject through apertures similar to the suction apertures 108 a temporary glue or polymer that adheres with tissues.

In some embodiments, the method 200 is performed during an annuloplasty procedure, as illustrated schematically in the sequence of FIGS. 20A to 20E and described in further details hereinbelow. In such embodiments, the target biological tissue 12 is a valve annulus 110 and/or tissue adjacent the valve annulus 110, for example a mitral valve annulus 110. In a specific embodiment, annuloplasty includes implanting at least two of the helicoidal members 16 around the valve annulus 110 and tightening the valve annulus 110 by pulling the at least two helicoidal members 16 towards each other, As illustrated in FIGS. 22B and 22C. The helicoidal member 16 then has the same shape before and after insertion in the target tissue. In yet other embodiments, as illustrated in FIG. 22A, the helicoidal member 16 goes around the whole valve annulus 110 in a closed loop, or partially around the valve annulus 110 in an arc segment shape, and tightening the valve annulus includes reducing a radius of curvature of the helicoidal member 16.

In other embodiments, the helicoidal members 16 do not require pulling as they inherently allow tightening of the valve annulus 110. In one such embodiment, the helicoidal member 16 includes a shape memory material and changes between a helicoidal member first configuration and a helicoidal member second configuration at a transition temperature, the transition temperature being between 20° C. and 37° C. The helicoidal member first and second configurations have different pitches. In the case of annuloplasty, the helicoidal member second configuration may have a smaller pitch than the helicoidal member first configuration. In another example, the helicoidal member 16a is used. The helicoidal member 16a has a pitch that varies between the helicoidal member proximal and distal ends 20 and 22. For example, the pitch is larger at the helicoidal member distal end 22 than at the helicoidal member proximal end 20. In such embodiments, threading the helicoidal member 16a will compress the tissue to tighten the valve annulus.

A specific case of the method 200 used for installing an anchor or a suture around the mitral valve annulus 110 and cinching the latter to reduce its size are shown schematically from a top view in FIGS. 21A to 21C. At first, as shown in FIG. 21A, the guide 26 is shaped and positioned to match the mitral valve annulus 110 shape and position, corresponding to step 210. Once in place, as seen in FIG. 21B, adhesion is activated and the anchor, in the form of the helicoidal member 16, is advanced over the guide 26 plunging into tissue, corresponding to steps 215 and 220. FIG. 21C illustrates an embodiment in which a wire 112 is pre-attached to the guide 26. When the guide 26 is removed the wire 112 tethers through the helicoidal member passageway 24. Once both end of wire 112 are accessible, they are tightened and tension is maintained by a locking clip 115 that is advanced over a loop of the wire 112 passing through the helicoidal member 16. This effectively shrinks the radius of curvature of the helicoidal member 16 and in consequence the orifice size for the valve.

In other embodiments, as seen in FIGS. 21D and 21E, the wire 112 has a clip 115 at its free extremity that prevents the wire end to go through the helicoidal member 16 (by being too large to enter the helicoidal member passageway 24 thus allowing to cinch the helicoidal member 16 by only pulling on one end of the wire 112. In some cases to reduce any gaps that can persist between wire 112, helicoidal member 16 and target biological tissue 12, a bigger wire diameter is used with an expansion capabilities provided by foam type material. This reduces possible blood damage created by sharp edges and small gaps. In yet another embodiment, as seen in FIG. 21F, the helicoidal member 16b is removed, leaving in place the suture thread 86 and hook 88 running along the path of anchoring. When the suture thread 86 is pulled, the same area reduction as in FIGS. 21A to 21E may be achieved, albeit with less parts remaining inside the patient.

In other embodiments, the wire that tightens the helicoidal members 16 doesn't form a loop, so each helicoidal members 16 can be tightened individually, i.e. the wire is attached to the distal end of an insert 92a to 92d, and a pull on the proximal end of the wire with a locking clip will reduce the size of the wire thus reducing the size of the helicoidal member 16.

FIGS. 24A to 24D illustrate some steps of this process in a different orientation, with the guide 26 viewed head on. In FIG. 24A, the guide 26 is positioned adjacent to the mitral valve annulus 110. Then, as shown in FIG. 24B, the guide 26 is adhered to the mitral valve annulus 110 and the helicoidal member 16 is advanced on the guide 26, as shown in FIGS. 24C and 24D. FIGS. 24A to 24D illustrate the guide 26 positioned in the atrium. As shown in FIG. 24E, the guide 26 may also be positioned in the ventricle.

FIGS. 23A to 23D illustrate the attachment of a prosthesis in the form of a valve 114 (shown in FIG. 23A for example) or 114a (shown in FIG. 23C for example) at the valve annulus 110. The valves 114 and 114a are typically secured the the valve annulus 110 while the biological defective valve is left in place. However, in other embodiments, the biological defective valve may be removed before the valve 114 or 114a is attached.

Referring to FIG. 23D, the valve 114 includes a valve leaflet 116 secured to a leaflet support 118. The leaflet support 118 has for example a substantially ellipsoidal transversal cross-sectional configuration and is substantially elongated. The leaflet support 118 may be provided, in some embodiments, with a central wire 120 usable to adjust its shape prior or after implantation. The leaflet support 118 is secured to a guide 26e defining a substantially flat valve supporting surface 122, opposed to the peripheral surface cooled portion 32. The leaflet support 118 also defines a substantially flat leaflet support attachment surface 124 facing the valve supporting surface 122 and secured thereto in any suitable manner, for example through a relatively weak adhesive or by using a few spaced apart circular wires going around the guide 26e (not shown in the drawings), among other possibilities.

As shown in FIG. 23A, the valve 114 is positioned substantially adjacent the valve annulus 110, for example in the atrium. The guide 26e has been omitted from FIG. 23A but is usually present. In some embodiments, two guides 26e are used to anchor the leaflet support 118 from both ends thereof simultaneously, each with a respective helicoidal member 16. However, using a single helicoidal member 16 is also within the scope of the invention. Once the valve 114 is suitably positioned, the helicoidal member(s) 16 is (are) advanced over the leaflet support 118 and into the tissue adjacent the valve annulus 110. The resulting configuration is illustrated schematically in FIG. 23B. In other embodiments, a tubular valve 114a, partially shown in FIG. 23C is used instead, but the remainder of the process is similar to the process described for valve 114.

More specifically, referring to FIG. 23E, a pair of guides 26 arcing in opposed directions are positioned adjacent the valve annulus 110. Then, the tubular valve 114a is positioned over the pre-existing valve, and the helicoidal members 16 are each advanced over a respective guide 26 to anchor the valve 114a to the adjacent tissue, as seen in FIG. 23F. Finally, as seen in FIG. 23G, the guides 26 are removed with the helicoidal members 16 remaining anchored in the patient. The tubular valve 114a is better seen in FIG. 23H. For delivery, the tubular valve 114a is rolled to form a generally annular shape and then folded in half with each half secured to a respective guide 26. When exiting the catheter 36, the guides 26 deploy, forming the shape shown in the drawings and the valve 114a unrolls.

In yet another example, placating two pieces of tissue together by means of the system 10 is illustrated schematically in FIGS. 25A to 25H. In this embodiment, the hook 88 and suture thread 86 are used. The guide 26 is first suitably positioned and adhered to the target biological tissue 12, in this case between two tissue portions 13, and the helicoidal member 16b is advanced over both tissue portions 13, as seen in FIGS. 25A and 25B. Then, the helicoidal member 16b is withdrawn leaving in place the suture thread 86, as see in the sequence of FIGS. 25C, 25D and 25E. Subsequently, the guide 26 is removed and the continuous suture thread 86 is left in place, as seen in FIG. 25F. To further reduce and eliminate any distance therebetween and secure both tissue portions 13 to each other, the suture thread 86 is pulled on as illustrated in FIGS. 25G and 25H.

The system 10 is manufactured using materials commonly used in the biomedical industry, such as stainless steel and polymers.

Although the present invention has been described hereinabove by way of preferred embodiments thereof, it can be modified, without departing from the spirit and nature of the subject invention as defined in the appended claims.

What is claimed is:

1. A surgical method using a guide to assist in insertion of a helicoidal member in a target biological tissue, the target biological tissue defining a target tissue exposed surface, the helicoidal member defining a helicoidal member longitudinal axis and substantially longitudinally opposed helicoidal member proximal and distal ends, a helicoidal member passageway extending longitudinally between the helicoidal member proximal and distal ends, the guide being substantially elongated and defining a guide tip, the method comprising:

abutting a substantially longitudinally extending portion of the guide against the target tissue exposed surface with the helicoidal member mounted thereto so that at least a portion of the guide is inserted in the helicoidal member passageway substantially parallel to the helicoidal member longitudinal axis;

adhering the substantially longitudinally extending portion of the guide to the target tissue exposed surface with the helicoidal member longitudinal axis substantially parallel to the target tissue exposed surface; and advancing the helicoidal member in the target biological tissue in a substantially helicoidal movement with the guide remaining substantially fixed relative to the target biological tissue;

wherein adhering the substantially longitudinally extending portion of the guide to the target tissue exposed surface includes cooling at least part of the guide to a predetermined temperature, the predetermined temperature being low enough to cause cryoadhesion between the substantially longitudinally extending portion of the guide and the target tissue exposed surface.

2. The method as defined in claim 1, wherein the predetermined temperature is low enough to allow cryoadhesion, but remains high enough and is applied for a duration short enough that substantially no irreversible physiological damages are caused to the target biological tissue.

3. The method as defined in claim 1, wherein the predetermined temperature is between 0° C. and −40° C.

4. The method as defined in claim 1, wherein the guide includes suction apertures in the substantially longitudinally extending portion of the guide and wherein adhering the substantially longitudinally extending portion of the guide to the target tissue exposed surface includes exerting a suction through the suction apertures.

5. The method as defined in claim 4, wherein the guide is inserted in a deformable sleeve, the sleeve being partially inserted in the suction apertures.

6. The method as defined in claim 1, wherein the helicoidal member is between the guide tip and the substantially longitudinally extending portion of the guide before adhering the substantially longitudinally extending portion of the guide to the target tissue exposed surface.

7. The method as defined in claim 1, wherein the substantially longitudinally extending portion of the guide is between the guide tip and helicoidal member before adhering the substantially longitudinally extending portion of the guide to the target tissue exposed surface.

8. The method as defined in claim 1, wherein the substantially longitudinally extending portion of the guide and the helicoidal member have at least portions thereof substantially in register with each other before adhering the substantially longitudinally extending portion of the guide to the target tissue exposed surface.

9. The method as defined in claim 1, further comprising detaching the guide from the target tissue exposed surface with the helicoidal member remaining in the target biological tissue and removing the guide from within the helicoidal member passageway.

10. The method as defined in claim 9, further comprising delivering an insert while advancing the helicoidal member so that when the helicoidal member remains in the target biological tissue, the helicoidal member engages the insert.

11. The method as defined in claim 10, wherein the insert includes a membrane.

12. The method as defined in claim 10, wherein the insert includes a resiliently deformable material.

13. The method as defined in claim 9, further comprising delivering a prosthesis while advancing the helicoidal member so that when the helicoidal member remains in the target biological tissue, the prosthesis is secured to the target biological tissue by the helicoidal member.

14. The method as defined in claim 13, wherein the prosthesis includes a cardiac valve.

15. The method as defined in claim 1, wherein the helicoidal member supports a distally provided hook to which a suture thread is secured, the hook being removable from the helicoidal member, the method further comprising
using the helicoidal member to insert the suture thread in a helicoidal configuration in the target biological tissue;
withdrawing the helicoidal member from the target biological tissue with the hook hooking the target biological tissue so that the hook and suture thread remain in the target biological tissue; and
pulling on the suture thread to tighten the suture thread.

16. The method as defined in claim 1, further comprising positioning the guide at a predetermined location along the target tissue exposed surface before adhering the substantially longitudinally extending portion of the guide to the target tissue exposed surface.

17. The method as defined in claim 1, further comprising adjusting the shape of the guide before adhering the substantially longitudinally extending portion of the guide to the target tissue exposed surface.

18. The method as defined in claim 1, further comprising
inserting a catheter in a mammal in which the target biological tissue is located so that a catheter distal tip of the catheter is substantially adjacent the target tissue exposed surface; and
advancing the guide in the catheter until at least part of the guide protrudes from the guide.

19. The method as defined in claim 1, wherein the target biological tissue is a valve annulus.

20. The method as defined in claim 19, comprising implanting at least two of the helicoidal members around the valve annulus and tightening the valve annulus by pulling the at least two helicoidal member towards each other.

21. The method as defined in claim 19 wherein the method includes implanting the helicoidal member around the valve annulus and tightening the valve annulus by reducing a radius of curvature of the helicoidal member.

22. The method as defined in claim 19 wherein the valve annulus is a mitral valve annulus.

23. The method as defined in claim 1, wherein the helicoidal member has the same shape before and after insertion in the target biological tissue.

24. The method as defined in claim 1, wherein the helicoidal member includes a shape memory material, the helicoidal member changing between a helicoidal member first configuration and a helicoidal member second configuration at a transition temperature, the transition temperature being between 20° C. and 37° C.

25. The method as defined in claim 24, wherein the helicoidal member first and second configurations have different pitches.

26. The method as defined in claim 1, wherein the helicoidal member has a pitch that varies between the helicoidal member proximal and distal ends.

27. The method as defined in claim 26, wherein the pitch is larger at the helicoidal member distal end than at the helicoidal member proximal end.

28. The method as defined in claim 1, where the substantially longitudinally extending portion of the guide adhered to the target tissue exposed surface is at the guide tip.

29. The method as defined in claim 1, where the substantially longitudinally extending portion of the guide adhered to the target tissue exposed surface is spaced apart therefrom longitudinally from the guide tip.

30. A surgical method using a guide to assist in insertion of a helicoidal member in a target biological tissue, the target biological tissue defining a target tissue exposed surface, the helicoidal member defining a helicoidal member longitudinal axis and substantially longitudinally opposed helicoidal member proximal and distal ends, a helicoidal member passageway extending longitudinally between the helicoidal member proximal and distal ends, the guide being substantially elongated and defining a guide tip, the method comprising:
abutting a substantially longitudinally extending portion of the guide against the target tissue exposed surface with the helicoidal member mounted thereto so that at least a portion of the guide is inserted in the helicoidal member passageway substantially parallel to the helicoidal member longitudinal axis;

adhering the substantially longitudinally extending portion of the guide to the target tissue exposed surface with the helicoidal member longitudinal axis substantially parallel to the target tissue exposed surface; and advancing the helicoidal member in the target biological tissue in a substantially helicoidal movement with the guide remaining substantially fixed relative to the target biological tissue;

wherein the helicoidal member is between the guide tip and the substantially longitudinally extending portion of the guide before adhering the substantially longitudinally extending portion of the guide to the target tissue exposed surface.

31. A surgical method using a guide to assist in insertion of a helicoidal member in a target biological tissue, the target biological tissue defining a target tissue exposed surface, the helicoidal member defining a helicoidal member longitudinal axis and substantially longitudinally opposed helicoidal member proximal and distal ends, a helicoidal member passageway extending longitudinally between the helicoidal member proximal and distal ends, the guide being substantially elongated and defining a guide tip, the method comprising:

abutting a substantially longitudinally extending portion of the guide against the target tissue exposed surface with the helicoidal member mounted thereto so that at least a portion of the guide is inserted in the helicoidal member passageway substantially parallel to the helicoidal member longitudinal axis;

adhering the substantially longitudinally extending portion of the guide to the target tissue exposed surface with the helicoidal member longitudinal axis substantially parallel to the target tissue exposed surface; and advancing the helicoidal member in the target biological tissue in a substantially helicoidal movement with the guide remaining substantially fixed relative to the target biological tissue;

wherein the substantially longitudinally extending portion of the guide and the helicoidal member have at least portions thereof substantially in register with each other before adhering the substantially longitudinally extending portion of the guide to the target tissue exposed surface.

32. A surgical method using a guide to assist in insertion of a helicoidal member in a target biological tissue, the target biological tissue defining a target tissue exposed surface, the helicoidal member defining a helicoidal member longitudinal axis and substantially longitudinally opposed helicoidal member proximal and distal ends, a helicoidal member passageway extending longitudinally between the helicoidal member proximal and distal ends, the guide being substantially elongated and defining a guide tip, the method comprising:

abutting a substantially longitudinally extending portion of the guide against the target tissue exposed surface with the helicoidal member mounted thereto so that at least a portion of the guide is inserted in the helicoidal member passageway substantially parallel to the helicoidal member longitudinal axis;

adhering the substantially longitudinally extending portion of the guide to the target tissue exposed surface with the helicoidal member longitudinal axis substantially parallel to the target tissue exposed surface;

advancing the helicoidal member in the target biological tissue in a substantially helicoidal movement with the guide remaining substantially fixed relative to the target biological tissue;

delivering an insert while advancing the helicoidal member so that when the helicoidal member remains in the target biological tissue, the helicoidal member engages the insert; and detaching the guide from the target tissue exposed surface with the helicoidal member remaining in the target biological tissue and removing the guide from within the helicoidal member passageway;

wherein the insert includes a resiliently deformable material.

33. A surgical method using a guide to assist in insertion of a helicoidal member in a target biological tissue, the target biological tissue defining a target tissue exposed surface, the helicoidal member defining a helicoidal member longitudinal axis and substantially longitudinally opposed helicoidal member proximal and distal ends, a helicoidal member passageway extending longitudinally between the helicoidal member proximal and distal ends, the guide being substantially elongated and defining a guide tip, the method comprising:

abutting a substantially longitudinally extending portion of the guide against the target tissue exposed surface with the helicoidal member mounted thereto so that at least a portion of the guide is inserted in the helicoidal member passageway substantially parallel to the helicoidal member longitudinal axis;

adhering the substantially longitudinally extending portion of the guide to the target tissue exposed surface with the helicoidal member longitudinal axis substantially parallel to the target tissue exposed surface;

advancing the helicoidal member in the target biological tissue in a substantially helicoidal movement with the guide remaining substantially fixed relative to the target biological tissue;

delivering a prosthesis while advancing the helicoidal member so that when the helicoidal member remains in the target biological tissue, the prosthesis is secured to the target biological tissue by the helicoidal member; and detaching the guide from the target tissue exposed surface with the helicoidal member remaining in the target biological tissue and removing the guide from within the helicoidal member passageway.

34. The method as defined in claim 33, wherein the prosthesis includes a cardiac valve.

35. A surgical method using a guide to assist in insertion of a helicoidal member in a target biological tissue, the target biological tissue defining a target tissue exposed surface, the helicoidal member defining a helicoidal member longitudinal axis and substantially longitudinally opposed helicoidal member proximal and distal ends, a helicoidal member passageway extending longitudinally between the helicoidal member proximal and distal ends, the guide being substantially elongated and defining a guide tip, the helicoidal member supporting a distally provided hook to which a suture thread is secured, the hook being removable from the helicoidal member, the method comprising:

abutting a substantially longitudinally extending portion of the guide against the target tissue exposed surface with the helicoidal member mounted thereto so that at least a portion of the guide is inserted in the helicoidal member passageway substantially parallel to the helicoidal member longitudinal axis;

adhering the substantially longitudinally extending portion of the guide to the target tissue exposed surface with the helicoidal member longitudinal axis substantially parallel to the target tissue exposed surface; and advancing the helicoidal member in the target biological tissue in a substantially helicoidal movement with the guide remaining substantially fixed relative to the target biological tissue;

using the helicoidal member to insert the suture thread in a helicoidal configuration in the target biological tissue;

withdrawing the helicoidal member from the target biological tissue with the hook hooking the target biological tissue so that the hook and suture thread remain in the target biological tissue; and pulling on the suture thread to tighten the suture thread.

36. A surgical method using a guide to assist in insertion of a helicoidal member in a target biological tissue, the target biological tissue defining a target tissue exposed surface, the helicoidal member defining a helicoidal member longitudinal axis and substantially longitudinally opposed helicoidal member proximal and distal ends, a helicoidal member passageway extending longitudinally between the helicoidal member proximal and distal ends, the guide being substantially elongated and defining a guide tip, the method comprising:

inserting a catheter in a mammal in which the target biological tissue is located so that a catheter distal tip of the catheter is substantially adjacent the target tissue exposed surface;

advancing the guide in the catheter until at least part of the guide protrudes from the guide abutting a substantially longitudinally extending portion of the guide against the target tissue exposed surface with the helicoidal member mounted thereto so that at least a portion of the guide is inserted in the helicoidal member passageway substantially parallel to the helicoidal member longitudinal axis;

adhering the substantially longitudinally extending portion of the guide to the target tissue exposed surface with the helicoidal member longitudinal axis substantially parallel to the target tissue exposed surface; and advancing the helicoidal member in the target biological tissue in a substantially helicoidal movement with the guide remaining substantially fixed relative to the target biological tissue.

37. A surgical method using a guide to assist in insertion of a helicoidal member in a target biological tissue, the target biological tissue defining a target tissue exposed surface, the helicoidal member defining a helicoidal member longitudinal axis and substantially longitudinally opposed helicoidal member proximal and distal ends, a helicoidal member passageway extending longitudinally between the helicoidal member proximal and distal ends, the guide being substantially elongated and defining a guide tip, the method comprising:

abutting a substantially longitudinally extending portion of the guide against the target tissue exposed surface with the helicoidal member mounted thereto so that at least a portion of the guide is inserted in the helicoidal member passageway substantially parallel to the helicoidal member longitudinal axis;

adhering the substantially longitudinally extending portion of the guide to the target tissue exposed surface with the helicoidal member longitudinal axis substantially parallel to the target tissue exposed surface; and advancing the helicoidal member in the target biological tissue in a substantially helicoidal movement with the guide remaining substantially fixed relative to the target biological tissue;

wherein the target biological tissue is a valve annulus.

38. The method as defined in claim 37, comprising implanting at least two of the helicoidal members around the valve annulus and tightening the valve annulus by pulling the at least two helicoidal member towards each other.

39. The method as defined in claim 37 wherein the method includes implanting the helicoidal member around the valve annulus and tightening the valve annulus by reducing a radius of curvature of the helicoidal member.

40. The method as defined in claim 37 wherein the valve annulus is a mitral valve annulus.

41. A surgical method using a guide to assist in insertion of a helicoidal member in a target biological tissue, the target biological tissue defining a target tissue exposed surface, the helicoidal member defining a helicoidal member longitudinal axis and substantially longitudinally opposed helicoidal member proximal and distal ends, a helicoidal member passageway extending longitudinally between the helicoidal member proximal and distal ends, the guide being substantially elongated and defining a guide tip, the method comprising:

abutting a substantially longitudinally extending portion of the guide against the target tissue exposed surface with the helicoidal member mounted thereto so that at least a portion of the guide is inserted in the helicoidal member passageway substantially parallel to the helicoidal member longitudinal axis;

adhering the substantially longitudinally extending portion of the guide to the target tissue exposed surface with the helicoidal member longitudinal axis substantially parallel to the target tissue exposed surface; and advancing the helicoidal member in the target biological tissue in a substantially helicoidal movement with the guide remaining substantially fixed relative to the target biological tissue;

wherein the helicoidal member includes a shape memory material, the helicoidal member changing between a helicoidal member first configuration and a helicoidal member second configuration at a transition temperature, the transition temperature being between 20° C. and 37° C.

42. A surgical method using a guide to assist in insertion of a helicoidal member in a target biological tissue, the target biological tissue defining a target tissue exposed surface, the helicoidal member defining a helicoidal member longitudinal axis and substantially longitudinally opposed helicoidal member proximal and distal ends, a helicoidal member passageway extending longitudinally between the helicoidal member proximal and distal ends, the guide being substantially elongated and defining a guide tip, the method comprising:

abutting a substantially longitudinally extending portion of the guide against the target tissue exposed surface with the helicoidal member mounted thereto so that at least a portion of the guide is inserted in the helicoidal member passageway substantially parallel to the helicoidal member longitudinal axis;

adhering the substantially longitudinally extending portion of the guide to the target tissue exposed surface with the helicoidal member longitudinal axis substantially parallel to the target tissue exposed surface; and advancing the helicoidal member in the target biological tissue in a substantially helicoidal movement with the guide remaining substantially fixed relative to the target biological tissue;

wherein the helicoidal member has a pitch that varies between the helicoidal member proximal and distal ends.

43. A surgical method using a guide to assist in insertion of a helicoidal member in a target biological tissue, the target biological tissue defining a target tissue exposed surface, the helicoidal member defining a helicoidal member longitudinal axis and substantially longitudinally opposed helicoidal member proximal and distal ends, a helicoidal member passageway extending longitudinally between the helicoidal member proximal and distal ends, the guide being substantially elongated and defining a guide tip, the method comprising:
- abutting a substantially longitudinally extending portion of the guide against the target tissue exposed surface with the helicoidal member mounted thereto so that at least a portion of the guide is inserted in the helicoidal member passageway substantially parallel to the helicoidal member longitudinal axis;
- adhering the substantially longitudinally extending portion of the guide to the target tissue exposed surface with the helicoidal member longitudinal axis substantially parallel to the target tissue exposed surface; and
- advancing the helicoidal member in the target biological tissue in a substantially helicoidal movement with the guide remaining substantially fixed relative to the target biological tissue;
- wherein the guide includes suction apertures in the substantially longitudinally extending portion of the guide and wherein adhering the substantially longitudinally extending portion of the guide to the target tissue exposed surface includes exerting a suction through the suction apertures, the guide being inserted in a deformable sleeve, the sleeve being partially inserted in the suction apertures.

* * * * *